United States Patent [19]

Fabre et al.

[11] Patent Number: 4,783,472

[45] Date of Patent: Nov. 8, 1988

[54] 1H,3H-PYRROL[1,2-c]THIAZOLE DERIVATIVES AND PHARMACEUTICAL COMPOSITIONS CONTAINING THEM

[75] Inventors: Jean-Louis Fabre; Claude James; Daniel Lavé, all of Paris, France

[73] Assignee: Rhone-Poulenc Sante, Courbevoie, France

[21] Appl. No.: 69,520

[22] Filed: Jul. 2, 1987

[30] Foreign Application Priority Data

Jul. 4, 1986 [FR] France .................. 86 09728

[51] Int. Cl.$^4$ .................. C07D 409/00; C07D 401/00; C07D 217/00; C07D 215/04
[52] U.S. Cl. .................................. 514/338; 546/270; 546/256; 546/144; 546/148; 546/149; 546/173; 546/274; 546/177; 514/307; 514/314
[58] Field of Search ............... 546/274, 256, 144, 148, 546/149, 173, 177, 270; 514/338, 307, 314

[56] References Cited

U.S. PATENT DOCUMENTS 4,500,532 2/1985 Loev et al. .................. 546/274

FOREIGN PATENT DOCUMENTS 0115979 3/1987 European Pat. Off. .......... 546/274

Primary Examiner—Alan L. Rotman
Assistant Examiner—Robert C. Whittenbaugh
Attorney, Agent, or Firm—Stevens, Davis, Miller & Mosher

[57] ABSTRACT

A compound of the general formula I;

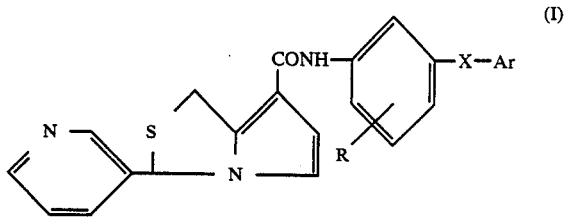

in which R is hydrogen or a halogen or an alkyl, alkyloxy, alkylthio, trifluoromethyl, amino, alkylamino, dialkylamino, hydroxy, cyano, carboxy, alkylsulphinyl, alkylsulphonyl, sulphamido, alkylsulphamido, dialkylsulphamido, carbamoyl, alkylcarbamoyl, dialkylcarbamoyl, phenylcarbamoyl, diphenylcarbamoyl, pyridylcarbamoyl, dipyridylcarbamoyl, benzyl, alkylcarbonyl, benzoyl, alkyloxycarbonyl, phenoxycarbonyl, alkylcarbonyloxy, benzoyloxy, alkylcarbonylamino, benzamido, phenyl, phenoxy or phenylthio group, X is oxygen or sulphur or an imino, alkylimino, phenylimino, benzylimino, sulphinyl, sulphonyl, carbonyl, carbonylmethylene, methylenecarbonyl, carbonylvinylene or vinylenecarbonyl group, or X represents a valency bond or a straight-chain alkylene group containing 1 to 4 carbon atoms and Ar is a phenyl, naphthyl, pyridyl, quinolinyl, isoquinolinyl, thienyl, benzothienyl, thieno[3,2-b]thien-2-yl or thieno[2,3-b]thien-2-yl group, it being possible for the group Ar to be unsubstituted or substituted with one or more halogen or alkyl, alkyloxy, alkylthio, trifluoromethyl, amino, alkylamino, dialkylamino, hydroxy, cyano, carboxy, alkylsulphinyl, alkylsulphonyl, sulphamido, alkylsulphamido, dialkylsulphamido, carbamoyl, alkylcarbamoyl, dialkylcarbamoyl, phenylcarbamoyl, diphenylcarbamoyl, pyridylcarbamoyl, dipyridylcarbamoyl, benzyl, alkylcarbonyl, benzoyl, alkyloxycarbonyl, phenoxycarbonyl, alkylcarbonyloxy, benzoyloxy, alkylcarbonylamino or benzamido group;

each alkyl moiety containing 1 to 4 straight- or branched-chain carbon atoms; the compound being in separate enantiomeric form or mixtures thereof or a pharmaceutically acceptable salt thereof is useful in the treatment of all the pathological conditions in which PAF-acether may be directly or indirectly implicated.

18 Claims, No Drawings

1H,3H-PYRROL[1,2-c]THIAZOLE DERIVATIVES AND PHARMACEUTICAL COMPOSITIONS CONTAINING THEM

The present invention provides compounds of the general formula I:

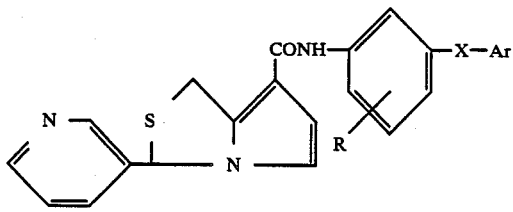

in which R is hydrogen or a halogen or an alkyl, alkyloxy, alkylthio, trifluoromethyl, amino, alkylamino, dialkylamino, hydroxy, cyano, carboxy, alkylsulphinyl, alkylsulphonyl, sulphamido, alkylsulphamido, dialkylsulphamido, carbamoyl, alkylcarbamoyl, dialkylcarbamoyl, phenylcarbamoyl, diphenylcarbamoyl, pyridylcarbamoyl, dipyridylcarbamoyl, benzyl, alkylcarbonyl, benzoyl, alkyloxycarbonyl, phenoxycarbonyl, alkylcarbonyloxy, benzoyloxy, alkylcarbonylamino, benzamido, phenyl, phenoxy or phenylthio group, X is oxygen or sulphur or an imino, alkylimino, phenylimino, benzylimino, sulphinyl, sulphonyl, carbonyl, carbonylmethylene, methylenecarbonyl, carbonylvinylene or vinylenecarbonyl group, or X represents a valency bond or a straight-chain alkylene group containing 1 to 4 carbon atoms and Ar is a phenyl, naphthyl, pyridyl, quinolinyl, isoquinolinyl, thienyl, benzothienyl, thieno[3,2-b]thien-2-yl or thieno[2,3-b]thien-2-yl group, it being possible for the group Ar to be unsubstituted or substituted with one or more halogen or alkyl, alkyloxy, alkylthio, trifluoromethyl, amino, alkylamino, dialkylamino, hydroxy, cyano, carboxy, alkylsulphinyl, alkylsulphonyl, sulphamido, alkylsulphamido, dialkylsulphamido, carbamoyl, alkylcarbamoyl, dialkylcarbamoyl, phenylcarbamoyl, diphenylcarbamoyl, pyridylcarbamoyl, dipyridylcarbamoyl, benzyl, alkylcarbonyl, benzoyl, alkyloxycarbonyl, phenoxycarbonyl, alkylcarbonyloxy, benzoyloxy, alkylcarbonylamino or benzamido group;

each alkyl moiety containing 1 to 4 straight- or branched-chain carbon atoms the compound being in separate enantiomeric form or mixtures thereof or a pharmaceutically acceptable salt thereof.

According to one aspect of the invention, the compounds of general formula (I) may be prepared by reacting an amine of general formula II:

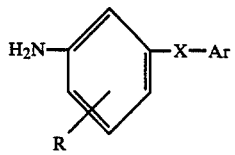

in which R, X and Ar are as defined above optionally in protected form, with a racemic or optically active acid of formula III:

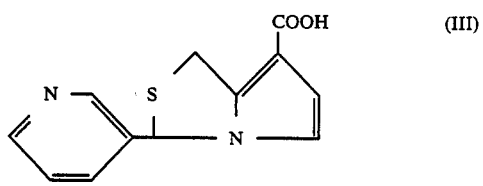

or a reactive derivative of this acid, isolating the product, removing any protecting groups present and, if required, converting the product into a pharmaceutically acceptable salt.

In fact, it is particularly advantageous to use the acid of formula (III) in an activated form such as the acid chloride or to react it with N,N'-carbonyldiimidazole or an alkyl chloroformate before condensing the amine of general formula (II).

In general, it is preferable to use the acid chloride and to carry out the reaction in an organic solvent such as chloroform, methylene chloride or dioxane at a temperature between 0° C. and the reflux temperature of the reaction mixture, in the presence of an acid acceptor, such as triethylamine.

The racemic acid of formula (III) may be prepared according to the method described in European patent No. 0,115,979.

The amines of general formula (II) may be prepared by applying or adapting the methods which are already described in the literature.

Because of the presence of an asymmetric carbon atom in position 3 of the pyrrolo[1,2-c]thiazole ring, the compounds of general formula I according to the invention can exist in the form of racemic compounds or in the form of enantiomers. The method described above generally leads to racemic products, but it is understood that the corresponding enantiomers may be obtained directly if the method is implemented operating with an acid of formula (III) which is optically active.

The optically active form of the acid of formula (III) may be prepared according to one of the following methods:

A. First method: An optically active ester with the corresponding specific rotation, of general formula:

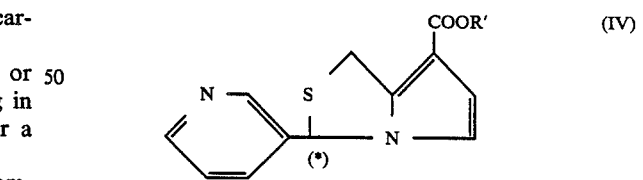

in which R' represents an alkyl radical containing 1 to 4 carbon atoms in straight- or branched-chain and the symbol * represents the sign + or the sign — depending on whether the product employed is dextrorotatory or levorotatory is saponified.

The saponification is generally carried out by any mild method known to the person skilled in the art, for the conversion of an ester into acid without racemizing the chiral centres present in the molecule. It is particularly advantageous to carry out the saponification with an alkali metal hydroxide such as sodium hydroxide or potassium hydroxide at a temperature between 20° and 50° C.

The ester of general formula (IV) may be obtained by reacting the reaction product of p-toluenesulphonyl chloride, triethylamine and the acid of formula:

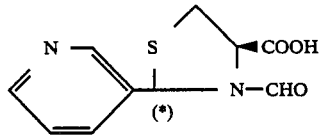

(V)

in which the symbol * has the same meaning as in the corresponding ester (IV) defined above, with the reaction product of triethylamine and an alkyl 2,3-dichloropropionate of general formula:

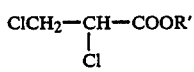

(VI)

in which R' is as defined above, in an organic solvent such as 1,2-dichloroethane or methylene chloride at a temperature between 20° C. and the reflux temperature of the reaction mixture.

The acid of general formula (V) may be obtained by reacting a mixture of formic acid and acetic anhydride with an acid of formula:

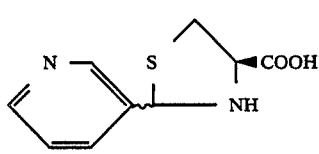

(VII)

and subsequently separating the dextrorotatory and the levorotatory forms operating according to conventional methods, e.g. by recrystallization and/or salt formation with optically active bases such as α-methylbenzylamine, separating these salts and releasing the corresponding acid.

B. Second method: The enantiomers of the acid of formula (III) are separated by any method known to the person skilled in the art, especially by a salt formation with an optically active base such as the optically active forms α-methylbenzylamine, recrystallizations of the salt obtained and decomposition of the latter with an acid such as hydrochloric acid.

According to another aspect of the invention, the compounds of general formula (I), may also be prepared by reacting the reaction product of p-toluenesulphonyl chloride, triethylamine and a racemic or optically active acid of formula (V) with the reaction product of triethylamine and a compound of general formula:

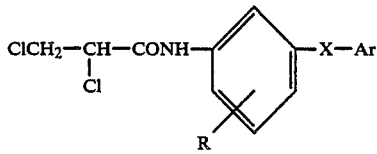

(VIII)

in which R, X and Ar are as defined above optionally in protected form, isolating the product, removing any protecting groups present and, if required, converting the product into a pharmaceutically acceptable salt.

The reaction is generally carried out in an organic solvent such as 1,2-dichloroethane or methylene chloride at a temperature between 20° C. and the reflux temperature of the reaction mixture.

The compounds of general formula (VIII) may be prepared by applying or adapting known methods in the literature, especially by reacting 2,3-dichloropropionyl chloride with an amine of general formula (II) defined as above, operating in toluene at a temperature between 20° C. and the reflux temperature of the reaction mixture.

It is understood that, in order to implement the methods described above, it may be necessary to introduce protective groups for some groups present in radicals R and Ar of the different compounds employed. The protective group may later be removed at the most appropriate stage in the synthesis.

Thus, when the radical Ar and/or R contains an amino or alkylamino group, the latter may be protected, e.g., by a tert-butyloxycarbonyl radical and then released, after reacting with an aqueous acid, e.g. with an aqueous solution of hydrochloric acid, or preferably with a solution containing hydrogen chloride gas dissolved in acetic acid. When the radical Ar and/or R contains a hydroxy group, the latter may advantageously be protected in the form of a tetrahydropyranyloxy or methoxymethyloxy radical, and then released, after reaction involving hydrolysis. When the radical Ar and/or R contains a carboxyl group, the latter may advantageously be protected in the form of an alkyl ester which may be saponified to give the corresponding acid, according to conventional methods.

The compounds of general formula (I) may be converted into an addition salt with acids by reacting with an acid in an organic solvent such as an alcohol, a ketone, an ether or a chlorinated solvent. The salt precipitates generally after concentrating the solution thereof; it is separated by filtration or decantation.

The compounds of general formula (I) containing an acid group in their molecule may be converted into metal salts or addition salts with nitrogenous bases, by any method known to the person skilled in the art for carrying out this salification without disturbing the rest of the molecule.

When a defined compound identified by its chemical name is referred to in the present description, if the nature of the isomers is not specifically mentioned, it is understood that it always refers to the corresponding racemic compound.

The compounds according to the invention and their addition salts have useful pharmacological properties combined with a low toxicity. They proved to be active at inhibitory concentrations (IC$_{50}$) of between 1 and 1,000 nM in the antagonism test for the binding of [$^3$H]-1-0-octadecyl-2-0-acetyl-3-ns-glycerophosphorylcholine (tritiated P.A.F.-acether [platelet activating factor]) to receptor sites on blood platelets according to the following technique:

(a) Preparation of washed rabbit platelets

Male New Zealand rabbits (hybrid HY 2000) weighing approximately 2.5 kg are punctured in the auricular artery. Blood is collected into a mixture of citric acid (1.9 mM), trisodium citrate (9 mM), monosodium phosphate (1.75 mM) and dextrose (5.6 mM). The blood is centrifuged at 120 g for 20 minutes at 15° C. Platelet-rich plasma (PRP) is thereby obtained. This plasma is centrifuged at 1,000 g for 15 minutes at 15° C. The platelet pellet thus obtained is washed first with the modified Tyrode's solution containing 0.35% of bovine serum albumin (BSA), 2 mMole per liter of $MgCl_2$, 0.2 mMole per liter of EGTA, and then with a Tyrode's solution without EGTA. The platelets are finally resuspended in a trial buffer (buffer A) with the following composition: NaCl (140 mM), KCl (2.7 mM), $NaH_2PO_4$ (0.4 mM), $MgCl_2$ (2 MM), $NaHCO_3$ (12 mM), Tris-HCl buffer (10 mM), dextrose (6.2 mM) and BSA (0.25%). The final concentration of the suspension is adjusted to $4.10^8$ platelets/cc with the buffer.

(b) Performance of the actual test

The buffer A described above, the product under study, the acetyl-tritiated PAF-acether (0.5 nMole; specific activity: 80 Ci/mMole) and the platelets obtained as described above ($0.5.10^8$ platelets) are introduced successively into a 5 cc tube so as to obtain a final volume of 0.5 cc and the mixture is incubated for one hour at 20° C. Buffer A (2 cc), cooled to 4° C., is then added and the contents of the tube are quickly filtered through a WHATMAN GF/C (trademark) filter and the tube is very quickly rinsed with buffer A (3×2 cc) cooled to 4° C. The filter is dried and placed in a vial containing liquid scintillant READY SOLV. MP (T. M. BECKMAN) (4.5 cc) and the radioactivity is measured with an LKB RACK BETA 1218 universal counter. The total bound radioactivity is thus determined. The specific binding of the tritiated PAF-acether is determined by subtracting the radioactivity remaining on the filter after adding 10 μMole of N-(3-methoxyphenyl)-3-(3-pyridyl)-1H,3H-pyrrolo[1,2-c]thiazole-7-carboxamide from the total bound radioactivity. For each product under study, the trial is repeated 3 times at increasing concentrations ranging from $10^{-10}$ to $10^{-4}$ M. For each product, the $IC_{50}$ is determined graphically by the log Probit analysis of the inhibition curve.

It is known that PAF-acether is involved in a large number of diseases and disorders such as allergic reactions (asthma or bronchitis) or inflammatory reactions of gastric and intestinal mucosae of different origins and especially the inflammatory reactions caused by radiations and by endotoxin-induced shocks and in disorders related to platelet agregation. The PAF-acether released during these disorders becomes bound to the specific receptors of this mediator. The test for binding to blood platelet receptors described above is one of the possible experimental models for studying the capacity of the products to bind to these receptors.

The compounds according to the invention displace the PAF-acether from their binding sites. Therefore, they enter into competition with it and antagonize the effects thereof. Thus, the compounds according to the invention have a therapeutic role in the treatment of the diseases and the conditions listed above.

Pyrrolothiazoles which have a certain inhibitory effect towards PAF-acether are already known from European patent No. 0,115,979, but the compounds according to the present invention become bound to platelet receptors at much lower doses and are therefore more capable of inhibiting the effects of PAF-acether.

Moreover, the products according to the invention have a low toxicity. Their oral $LD_{50}$ is generally between 300 and 900 mg/kg in mice.

The compounds of general formula (I) in which R represents a hydrogen or halogen atom or an alkyloxy or dialkylamino radical, X represents an oxygen or sulphur atom or an imino, carbonyl, carbonylmethylene or vinylenecarbonyl radical, or alternatively, it represents a methylene radical, and Ar represents a phenyl, naphthyl, pyridyl or 2-thienyl radical, it being possible for these radicals to be unsubstituted or substituted with a halogen atom or an alkyl, alkyloxy, dialkylamino, carboxy or alkyloxycarbonyl radical, are particularly valuable.

The products of general formula (I) in which R represents a hydrogen atom, X represents an oxygen atom or a carbonyl radical and Ar represents a phenyl or pyridyl radical, it being possible for these radicals to be unsubstituted or substituted with a halogen atom or an alkyl or alkyloxy radical, are more particularly valuable.

The following products are of a very particular value:

(+)-N-(3-benzoylphenyl)-3-(3-pyridyl)-1H,3H-pyrrolo[1,2-c]thiazole-7-carboxamide N-(3-benzoylphenyl)-3-(3-pyridyl)-1H,3H-pyrrolo[1,2,-c]thiazole-7-carboxamide N-(3-phenoxyphenyl)-3-(3-pyridyl)-1H,3H-pyrrolo[1,2,c]thiamole-7-carboxamide N-[3-(2-methylphenoxy)phenyl]-3-(3-pyridyl)-1H,3H-pyrrolo[1,2-c]thiazole-7-carboxamide N-[3-(3-pyridyloxy)phenyl]-3-(3-pyridyl)-1H, 3H-pyrrolo[1,2-c]thiazole-7-carboxamide N-[3-(3-methylphenoxy)phenyl]-3-(3-pyridyl)-1H,3H-pyrrolo[1,2-c]thiazole-7-carboxamide N-[3-(3-methylbenzoyl)phenyl]-3-(3-pyridyl)-1H,3H-pyrrolo[1,2-c]thiazole-7-carboxamide N-[3-(4-chlorophenoxy)phenyl]-3-(3-pyridyl)-1H,3H-pyrrolo[1,2-c]thiazole-7-carboxamide and N-[3-nicotinoylphenyl]-3-(3-pyridyl)-1H,3H-pyrrolo[1,2-c]thiazole-7-carboxamide.

In general, the compounds according to the invention which are the most valuable are those which are in a racemic form and the optical isomers of the dextrorotatory form.

For therapeutic use, the compounds of general formula (I) may be used as such or, when appropriate, in the form of pharmaceutically acceptable salts, i.e. salts which are non-toxic at the doses of use.

As pharmaceutically acceptable salts, there may be mentioned addition salts with inorganic acids, such as hydrochlorides, sulphates, nitrates, phosphates or addition salts with organic acids, such as acetates, propionates, succinates, benzoates, fumarates, malates, methanesulphonates, isethionates, theophillineacetates, salicylates, phenolphthalinates methylene-bis-β-oxynaphthoates or substitution derivatives of these compounds. There may also be mentioned, when they can exist, alkali metal salts such as sodium, potassium or lithium salts, alkaline earth metal salts such as calcium or magnesium salts, and addition salts with organic bases such as ethanolamine or lysine salts.

The following examples, given in a non-limiting way, show how the invention can be put into practice.

EXAMPLE 1

7-chloroformyl-3-(3-pyridyl)-1H,3H-pyrrolo[1,2-c]thiazole hydrochloride (4.5 g) is added, at a temperature between 60° C. and 68° C., to a solution of 3-phenoxyaniline (2.8 g) and triethylamine (3.05 g) in dioxane (100 cc) heated to a temperature in the vicinity of 60° C., in the course of 5 minutes. The suspension obtained is heated, with stirring, at a temperature in the vicinity of 100° C. for 6 hours and 15 minutes and is then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (250 cc) and the solution obtained is washed twice with distilled water (200 cc in total), twice with an aqueous 4N sodium hydroxide solution (200 cc in total) and twice with distilled water (200 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. Crude product (6.7 g) is thereby obtained. This product is dissolved in boiling isopropanol (25 cc). Decolourizing charcoal (0.5 g) is added to the solution obtained and the suspension is filtered in the heated state. The filtrate is cooled at a temperature in the vicinity of 4° C. for 3 hours. The crystals formed are separated by filtration, washed 4 times with ispropanol (20 cc in total) and then 3 times with diethyl ether (75 cc in total) and dried under reduced pressure (20 mm Hg; 2.7 kPa) at a temperature in the vicinity of 20° C. in the presence of potassium hydroxide pellets. N-(3-phenoxyphenyl)-3(3-pyridyl)-1H,3H-pyrrolo[1,2-c]thiazole-7-carboxamide (2.1 g) in the form of creamcoloured crystals, m.p. 144° C., is thereby obtained.

The 3-phenoxyaniline may be prepared according to the method described by F. ULLMANN and P. SPONAGEL, Annalen, 350, 83 (1906).

The 7-chloroformyl-3-(3-pyridyl)-1H,3H-pyrrolo[1,2-c]thiazole hydrochloride is prepared according to the method described in European patent No. 0,115,979.

EXAMPLE 2

Hydrochloride of the acid chloride derived from (+)-3-(3-pyridyl)-1H,3H-pyrrolo[1,2-c]thiazole-7-carboxylic acid (24.5 g) is added, at a temperature between 60° and 72° C., to a solution of 3-aminobenzophenone (16.1 g) and triethylamine (16.5 g) in dioxane (420 cc) which is heated to a temperature in the vicinity of 60° C., in the course of 5 minutes. The suspension obtained is heated, with stirring, at a temperature in the vicinity of 100° C. for 6 hours and 30 minutes and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in ethyl acetate (750 cc). The solution obtained is washed 3 times with distilled water (800 cc in total), twice with a saturated aqueous sodium bicarbonate solution (600cc in total) and twice with distilled water (600 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 60° C. Crude product (36 g) is thereby obtained, which is dissolved in a boiling ethanol:water (85:15 by volume) mixture (200 cc). Decolourizing charcoal (0.5 g) is added to the solution obtained and the suspension is filtered in the heated state. The filtrate is cooled at a temperature in the vicinity of 20° C. for 3 hours. The crystals formed are separated by filtration, washed 3 times with an ethanol: water (85:15 by volume) mixture (75 cc in total) and 4 times with diethylether (200 cc in total) and then dried under reduced pressure (20 mm Hg; 2.7 kPa) at a temperature in the vicinity of 20° C. in the presence of potassium hydroxide pellets. (+)-N-(3-benzoylphenyl)-3-(3-pyridyl)-1H,2H-pyrrolo[1,2-c]thiazole-7-carboxamide in the hydrated state (20.7 g), in the form of cream-coloured crystals, m.p. 109° C. is thereby obtained.

$[\alpha]_D^{20} = 87.5° \pm 1°$ (c=1.02; dimethylformamide)

The hydrochloride of the acid chloride derived from (+)-3-(3-pyridyl)-1H,3H-pyrrolo[1,2-c]thiazole-7-carboxylic acid is prepared as follows: a suspension of (+)-3-(3-pyridyl)-1H,3H-pyrrolo[1,2-c]thiazole-7-carboxylic acid (20.9 g) in a mixture of thionyl chloride (52.1 g), dimethylformamide (0.1 cc) and 1,2-dichloroethane (290 cc) is heated at a temperature in the vicinity of 80° C. for 3 hours. After cooling to a temperature in the vicinity of 20° C., the crystals are separated by filtration, washed 3 times with 1,2-dichloroethane (150 cc in total), 3 times with diethylether (150 cc) and then dried under reduced pressure (20 mm Hg; 2.7 kPa) at a temperature in the vicinity of 20° C. The hydrochloride of the acid chloride derived from (+)-3-(3-pyridyl)-1H,3H-pyrrolo-[1,2-c]thiazole-7-carboxylic acid (24.5 g) in the form of cream-coloured crystals, m.p. 175° C., is thereby obtained.

The (+)-3-(3-pyridyl)-1H,3H-pyrrolo[1,2-c]thiazole-7-carboxylic acid may be obtained as follows, according to one or the other of the following methods:

A. First method: A solution of ethyl (+)-3-(3-pyridyl)-1H,3H-pyrrolo[1,2-c]thiazole-7-carboxylate (19.5 g) and potassium hydroxide pellets (11.9 g) in a mixture of ethanol (70 cc) and distilled water (70 cc) is heated at a temperature in the vicinity of 40° C. for 14 hours. The solvent is evaporated off under reduced pressure (20 mm Hg; 2.7 kPa) at a temperature in the vicinity of 40° C. The residue is dissolved in distilled water (200 cc) and the solution obtained is adjusted to a pH in the vicinity of 4 by adding an aqueous 1N hydrochloric acid solution (250 cc) and stirred at a temperature in the vicinity of 20° C. for 1 hour. The crystals formed are separated by filtration, washed 5 times with distilled water (250 cc in total), 5 times with ethanol (150 cc in total) and 3 times with diethylether (90 cc in total) and then dried under reduced pressure (20 mm Hg; 2.7 kPa) at a temperature in the vicinity of 20° C. in the presence of potassium hydroxide pellets. Crude product (14.1 g), m.p. 210° C., is obtained. This product is dissolved in boiling ethanol (420 cc); decolourizing charcoal (0.5 g) is added to the solution obtained and the suspension is filtered in the heated state. The filtrate is cooled at a temperature in the vicinity of 4° C. for 16 hours. The crystals formed are separated by filtration, washed 3 times with ethanol (90 cc in total) and 3 times with diethyl ether (150 cc in total) and then dried under reduced pressure (20 mm Hg; 2.7 kPa) at a temperature in the vicinity of 20° C. (+)-3-(3-pyridyl)-1H,3H-pyrrolo[1,2-c]thiazole-7-carboxylic acid (10.3 g) in the form of cream-coloured crystals, m.p. 210° C. is thereby obtained.

$[\alpha]_D^{20} = +163° \pm 1.6°$ (c=1.08; 1N sodium hydroxide)

The ethyl (+)-3-(3-pyridyl)-1H,3H-pyrrolo[1,2-c]thiazole-7-carboxylate may be prepared as follows: triethylamine (11.2 g) is added, at a temperature between 20° and 27° C., to a suspension of (2R,4R)-N-formyl-2-(3-pyridyl)thiazolidine-4-carboxylic acid (23.8 g) in 1,2-dichloroethane (90 cc), in the course of 2 minutes. The suspension obtained is stirred at a temperature in the vicinity of 20° C. for 1 hour and the solution obtained is added, at a temperature in the vicinity of 20° C., to a solution of para-toluenesulphonyl chloride (21 g) in 1,2-dichloroethane (110 cc), in the course of 50 minutes. A cloudy solution is obtained (solution A). In a separate operation, triethylamine (4 g) is added, at a temperature between 20° and 30° C., to a solution of ethyl 2,3-dichloropropionate (18.6 g) in 1,2-dichloroethane (100 cc), in the course of 15 minutes. The solution A prepared previously is added, at a temperature between 20° and 36° C., to the suspension (suspension B) obtained which is stirred at a temperature in the vicinity of 20° C. for 50 minutes, in the course of 50 minutes. The suspension obtained is stirred for 1 hour and 40 minutes at a temperature in the vicinity of 40° C. and then for 20 minutes at a temperature in the vicinity of 60° C. Distilled water (100 cc) is added to the suspension obtained, after cooling it to a temperature in the vicinity of 20° C. The organic phase is separated, washed 3 times with distilled water (300 cc in total), twice with a saturated aqueous sodium bicarbonate solution (300 cc in total) and then twice with distilled water (300 cc in total) dried over anhydrous magnesium sulphate, treated with decolourizing charcoal (0.5 g), filtered and concentrated to dryness under reduced pressure (20 mm Hg; 2.7 kPa) at a temperature in the vicinity of 60° C. Crude product (25.6 g) is obtained, which is dissolved in ethyl acetate (250 cc). The solution obtained is extracted 3 times with an aqueous 2N hydrochloric solution (300 cc in total). The aqueous extracts are combined, washed with ethyl acetate (250 cc) and adjusted to a pH in the vicinity of 8 by adding sodium bicarbonate. The suspension obtained is extracted a first time with a mixture of diethylether (250 cc) and ethyl acetate (250 cc) and then 3 times with ethyl acetate (450 cc in total). The organic extracts are combined, washed twice with distilled water (300 cc in total), dried over anhydrous magnesium sulphate, treated with decolourizing charcoal (0.5 g), filtered, treated with silica (0.020–0.045 mm; 30 g), filtered and concentrated to dryness under reduced pressure (20 mm Hg; 2.7 kPa) at a temperature in the vicinity of 60° C. Ethyl (+)-3-(3-pyridyl)-1H,3H-pyrrolo[1,2-c]thiazole-7-carboxylate (19.6 g), in the form of an orange-coloured oil is thereby obtained. Rf=0.5 (silica gel thin layer chromatography; eluant: ethyl acetate);

$[\alpha]_D^{20} = +115° \pm 1°$ (c=1.51; dimethylformamide).

The ethyl 2,3-dichloropropionate may be prepared according to the method described in Japanese patent No. 81/87,531 [Chem. Abstr. 95, 203335, (1981)].

The (2R,4R)-N-formyl-2-(3-pyridyl)thiazolidine-4-carboxylic acid may be obtained as follows: acetic anhydride (340 g) is added, at a temperature in the vicinity of 10° C., to formic acid (420 cc), in the course of 25 minutes. The solution obtained is stirred at a temperature in the vicinity of 10° C. for 30 minutes and (2RS,4R)-2-(3-pyridyl)thiazolidine-4-carboxylic acid (233 g) is then added to it, at a temperature in the vicinity of 10° C., in the course of 50 minutes. The solution obtained is stirred at a temperature in the vicinity of 10° C. for 30 minutes and then at a temperature in the vicinity of 20° C. for 16 hours. The solvent is evaporated off under reduced presure (20 mm Hg; 2.7 kPa) at a temperature in the vicinity of 60° C. The residue obtained is suspended in boiling ethanol (2600 cc). The suspension obtained is cooled at a temperature in the vicinity of 4° C. for 2 hours. The crystals formed are separated by filtration, washed twice with ethanol cooled to a temperature in the vicinity of 4° C. (530 cc in total) and air-dried. A product (245 g) with a melting point of 230° C. is thereby obtained. A part of this product (60 g is dissolved in boiling aqueous 50% ethanol (540 cc). The solution obtained is cooled at a temperature in the vicinity of 10° C. for 2 hours. The crystals formed are separated by filtration, washed 3 times with ethanol (300 cc in total) and 3 times with diethyl ether (450 cc) and then dried under reduced pressure (20 mm Hg; 2.7 kPa) at a temperature in the vicinity of 20° C. in the presence of potassium hydroxide pellets. (2R,4R)-N-formyl-2-(3-pyridyl)thiazolidine-4-carboxylic acid (48.2 g), in the form of white crystals, m.p. 250° C., is thereby obtained.

$[\alpha]_D^{20} = +100° \pm 1°$ (c=1.37; 1N sodium hydroxide).

The (2RS,4R)-2-(3-pyridyl)thiazolidine-4-carboxylic acid may be prepared according to A. BANASHEK and M. I. SHCHUKINA, J. Gen. Chem. U.S.S.R., 31, 1374 (1961); Chem. Abstr. 55, 24739h, (1961).

B. Second method: (±)-3-(3-pyridyl)-1H,3H-pyrrolo[1,2-c]thiazole-7-carboxylic acid (200 g) and L(−)α-methylbenzylamine (147 g) are dissolved in boiling isopropanol (1,000 cc). Decolourizing charcoal (0.5 g) is added to the solution obtained and the suspension is filtered in the heated state. The filtrate is cooled at a temperature in the vicinity of 20° C. for 16 hours. The crystals formed are separated by filtration, washed 3 times with isopropanol cooled to a temperature in the vicinity of 4° C. (450 cc in total) and 3 times with diethyl ether (600 cc in total) and then dried under reduced pressure (20 mm Hg; 2.7 kPa) at a temperature in the vicinity of 20° C. in the presence of potassium hydroxide pellets. A product (134.6 g) is obtained, which is dissolved in boiling isopropanol (500 cc). Decolourizing charcoal (0.5 g) is added to the solution obtained and the suspension is filtered in the heated state. The filtrate is cooled at a temperature in the vicinity of 20° C. for 16 hours. The crystals formed are separated by filtration, washed 3 times with isopropanol cooled to a temperature in the vicinity of 4° C. (300 cc in total) and twice with diethyl ether (400 cc) and then dried under reduced pressure (20 mm Hg; 2.7 kPa) at a temperature in the vicinity of 20° C. in the presence of potassium hydroxide pellets. A product (88.3 g) is obtained, which is dissolved in boiling isopropanol (500 cc); the solution obtained is filtered in the heated state and the filtrate is cooled at a temperature in the vicinity of 4° C. for 16 hours. The crystals formed are separated by filtration, washed twice with isopropanol cooled to a temperature in the vicinity of 4° C. (100 cc in total) and 3 times with diethyl ether (300 cc in total) and then dried under reduced pressure (20 mm Hg; 2.7 kPa) at a temperature in the vicinity of 20° C. in the presence of potassium hydroxide pellets. (+)-3-(3-pyridyl)-1H,3H-pyrrolo[1,2-c]thiazole-7-carboxylic acid L(−)α-methylbenzylamine salt (77.3 g), in the form of cream-coloured crystals, m.p. 154° C., is obtained.

$[\alpha]_D^{20} = +110° \pm 2°$ (c=1.01; water)

This product is dissolved in distilled water (600 cc) at a temperature in the vicinity of of 65° C. The solution obtained is filtered in the heated state and cooled to a temperature in the vicinity of 10° C. and adjusted to a pH in the vicinity of 3.5 by adding concentrated hydrochloric acid at a temperature between 10° and 15° C. The crystals formed are separated by filtration, washed 3 times with distilled water (600 cc in total), twice with ethanol (160 cc in total) and with diethyl ether (200 cc in total) and then dried under reduced pressure (20 mm Hg; 2.7 kPa) at a temperature in the vicinity of 20° C. in the presence of potassium hydroxide pellets. A product (48 g) is obtained, which is dissolved in boiling ethanol (1,000 cc); decolourizing charcoal (0.5 g) is added to the solution obtained and the suspension is filtered in the heated state. The filtrate obtained is cooled at a temperature in the vicinity of 4° C. for 2 hours. The crystals formed are separated by filtration, washed twice with ethanol cooled to a temperature in the vicinity of 4° C.

(60 cc in total), then twice with diethyl ether (200 cc) and then dried under reduced pressure (20 mm Hg; 2.7 kPa) at a temperature in the vicinity of 20° C. in the presence of potassium hydroxide pellets. (+)-3-(3-pyridyl)1H,3H-pyrrolo[1,2-c]thiazole-7-carboxamide (42.5 g) in the form of yellow crystals, m.p. 210° C., is thereby obtained.

$[\alpha]_D^{20} = +168° \pm 2°$; (c=1.02; 1N NaOH)

The (+)-3-(3-pyridyl)-1H,3H-pyrrolo[1,2-c]thiazole-7-carboxylic acid may be prepared according to the method described in European patent No. 0,115,979.

EXAMPLE 3

Triethylamine (6.7 g) is added, at a temperature between 20° and 27° C., to a suspension of (2R,4R)-N-formyl-2-(3-pyridyl)thiazolidine-4-carboxylic acid (14.3 g) in 1,2-dichloroethane (60 cc), in the course of 3 minutes. The suspension obtained is stirred at a temperature in the vicinity of 20° C. for 20 minutes and the solution obtained is added, at a temperature between 22° and 26° C., to a solution of para-toluenesulphonyl chloride (12.6 g) in 1,2-dichloroethane (70 cc) in the course of 1 hour. A fine suspension (suspension A) is obtained. In a separate operation, triethylamine (20 g) is added, at a temperature between 20° and 30° C., to a solution of N-(benzoylphenyl)-2,3-dichloropropionamide (19.3 g) in 1,2-dichloroethane (100 cc) in the course of 15 minutes. A suspension (suspension B) is thereby obtained, which is stirred at a temperature in the vicinity of 20° C. for 16 hours. The suspension A prepared previously is added, at a temperature between 22° and 40° C., to this suspension B in the course of 10 minutes. The new suspension obtained is heated at a temperature in the vicinity of 86° C. for 1 hour. After cooling to a temperature in the vicinity of 20° C., the reaction mixture is washed 3 times with distilled water (600 cc in total). The organic phase is separated, dried over anhydrous magnesium sulphate, treated with decolourizing charcoal (0.5 g), filtered and concentrated to dryness under reduced pressure (20 mm Hg; 2.7 kPa) at a temperature in the vicinity of 60° C. A product (29.3 g) is obtained, which is dissolved in ethyl acetate (500 cc); the solution obtained is treated with decolourizing charcoal (0.5 g) and with silica (0.020–0.045 mm; 30 g), filtered and concentrated to dryness under reduced pressure (20 mm Hg; 2.7 kPa) at a temperature in the vicinity of 60° C. A crude product (25.5 g) is obtained, which is dissolved in a boiling mixture (130 cc) of ethanol and water (85:15 by volume). Decolourizing charcoal (0.5 g) is added to the solution obtained and the suspension is filtered in the heated state. The filtrate is cooled at a temperature in the vicinity of 20° C. for 16 hours. The crystals formed are separated by filtration, washed twice with a mixture (60 cc in total) of ethanol and water (85:15 by volume) and 3 times with diethyl ether (150 cc in total) and then dried under reduced pressure (20 mm Hg; 2.7 kPa) at a temperature in the vicinity of 20° C. in the presence of potassium hydroxide pellets. (+)-N-(3-benzoylphenyl)-3-(3-pyridyl)-1H,3H-pyrrolo[1,2-c]thiazole-7-carboxamide (13.75 g) in the hydrated state, in the form of cream-coloured crystals, m.p. 110° C., is thereby obtained.

$[\alpha]_D^{20} = +88.2° \pm 1°$ (c=1.02; dimethylformamide)

The (2R,4R)-N-formyl-2-(3-pyridyl)thiazolidine-4-carboxylic acid may be prepared as mentioned in Example 2.

The N-(3-benzoylphenyl)-2,3-dichloropropionamide may be prepared as follows: a solution of 2,3-dichloropropionyl chloride (24.2 g) in toluene (80 cc) is added, at a temperature between 60° and 105° C., to a solution of 3-aminobenzophenone (29.6 g) in toluene (400 cc), in the course of 20 minutes. The solution obtained is heated at a temperature in the vicinity of 110° C. for 3 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in boiling isopropyl ether (250 cc). The solution obtained is cooled at a temperature in the vicinity of 20° C. for 16 hours. The crystals formed are separated by filtration, washed 3 times with isopropyl ether (300 cc in total) and dried under reduced pressure (20 mm Hg; 2.7 kPa) at a temperature in the vicinity of 20° C. in the presence of potassium hydroxide pellets. N-(3-benzoylphenyl)-2,3-dichloropropionamide (38.9 g) in the form of cream-coloured crystals, m.p. 92° C., is thereby obtained.

The 3-aminobenzophenone may be prepared according to R. GEIGY and W. KOENIGS, Ber., 18, 2400 (1885).

EXAMPLE 4

7-Chloroformyl-3-(3-pyridyl)-1H,3H-pyrrolo[1,2-c]thiazole hydrochloride (9 g) is added, at a temperature in the vicinity of 60° C., to a solution of 3-(4-chlorophenoxy)aniline (6.6 g) and triethylamine (6.1 g) in dioxane (200 cc) heated to a temperature in the vicinity of 60° C., in the course of 25 minutes. The suspension obtained is heated, with stirring, at a temperature in the vicinity of 100° C. for 5 hours and then stirred at a temperature in the vicinity of 20° C. for 16 hours. The solvent is evaporated off under reduced pressure (10 mm Hg; 2.7 kPa) at a temperature in the vicinity of 65° C. The residue is dissolved in methylene chloride (400 cc) and the solution obtained is washed twice with distilled water (200 cc in total), twice with an aqueous 1N sodium hydroxide solution (200 cc in total) and 5 times with distilled water (500 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. A product (13 g) is thereby obtained, which is chromatographed on a 3 cm diameter column containing silica (0.063–0.2 mm; 120 g). Elution is carried out with mixtures of methylene chloride and methanol, collecting 300 cc fractions. The first 5 fractions originating from elution with pure methylene chloride are discarded. The following 9 fractions originating from elution with a methylene chloride:methanol (99:1 by volume) mixture are combined and concentrated to dryness under reduced pressure (20 mm Hg; 2.7 kPa) at a temperature in the vicinity of 50° C. A crude product (9.4 g) is thereby obtained, which is dissolved in boiling isopropanol (100 cc). Decolourizing charcoal (0.5 g) is added to the solution obtained and the suspension is filtered in the heated state. The filtrate obtained is cooled at a temperature in the vicinity of 4° C. for 16 hours. The crystals formed are separated by filtration, washed twice with isopropanol cooled to a temperature in the vicinity of 4° C. (20 cc in total) and twice with diethyl ether (40 cc in total) and then dried under reduced pressure (20 mm Hg; 2.7 kPa) at a temperature in the vicinity of 20° C. in the presence of potassium hydroxide pellets. N-[3-(4-chlorophenoxy)phenyl]-3-(3-pyridyl)-1H,3H-pyrrolo[1,2-c]thiazole-7-carboxamide (6.5 g) in the form of cream-coloured crystals, m.p. 140° C., is thereby obtained.

The 3-(4-chlorophenoxy)aniline may be prepared according to K. IKAWA, J. Pharm. Soc. Jap., 79, 269 (1959).

The 7-chloroformyl-3-(3-pyridyl)-1H,3H-pyrrolo[1,2-c]thiazole hydrochloride is prepared according to the method described in European patent No. 0,115,979.

EXAMPLE 5

7-Chloroformyl-3-(3-pyridyl)-1H,3H-pyrrolo[1,2-c]thiazole hydrochloride (9 g) is added, at a temperature between 61° and 65° C., to a solution of 3-(2-methylphenoxy)aniline (6 g) and triethylamine (6.1 g) in dioxane (150 cc) which is heated to a temperature in the vicinity of 60° C., in the course of 35 minutes. The suspension obtained is heated, with stirring, at a temperature in the vicinity of 100° C. for 6 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (400 cc). The solution obtained is washed twice with distilled water (200 cc in total), twice with an aqueous 1N sodium hydroxide solution (200 cc in total) and 5 times with distilled water (500 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. A crude product (7 g) is thereby obtained, which is dissolved in boiling acetonitrile (100 cc). Decolourizing charcoal (0.5 g) is added to the solution obtained and the suspension is filtered in the heated state. The filtrate is cooled at a temperature in the vicinity of 4° C. for 1 hour. The crystals formed are separated by filtration, washed twice with acetonitrile cooled to a temperature in the vicinity of 4° C. (20 cc in total) and twice with diethyl ether (20 cc in total) and then dried under reduced pressure (20 mm Hg; 2.7 kPa) at a temperature in the vicinity of 20° C. in the presence of potassium hydroxide pellets. N-[3-(2-methylphenoxy)phenyl]-3-(3-pyridyl)-1H,3H-pyrrolo[1,2-c]thiazole-7-carboxamide (3.6 g), in the form of white crystals, m.p. 180° C. is thereby obtained.

The 3-(2-methylphenoxy)aniline may be prepared according to the method described in Dutch patent No. 66/2,994.

The 7-chloroformyl-3-(3-pyridyl)-1H,3H-pyrrolo[1,2-c]thiazole hydrochloride is prepared according to the method described in European patent No. 0,115,979.

EXAMPLE 6

7-Chloroformyl-3-(3-pyridyl)-1H,3H-pyrrolo[1,2-c]thiazole hydrochloride (9 g) is added, at a temperature between 60° and 64° C., to a solution of 3-(3-methylphenoxy)aniline (6 g) and triethylamine (6.1 g) in dioxane (200 cc) which is heated to a temperature in the vicinity of 60° C., in the course of 15 minutes. The suspension obtained is heated, with stirring, at a temperature in the vicinity of 100° C. for 4 hours and 30 minutes and then stirred at a temperature in the vicinity of 20° C. for 16 hours. The solvent is evaporated off under reduced pressure (20 mm Hg; 2.7 kPa) at a temperature in the vicinity of 60° C. The residue obtained is dissolved in methylene chloride (350 cc) and the solution obtained is washed twice with distilled water (200 cc in total), twice with an aqueous 1N sodium hydroxide solution (200 cc in total) and 5 times with distilled water (500 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. A crude product (13 g) is thereby obtained. This product is dissolved in boiling acetonitrile (50 cc). Decolourizing charcoal (0.5 g) is added to the solution obtained and the suspension is filtered in the heated state. The filtrate is cooled at a temperature in the vicinity of 4° C. for 2 hours. The crystals formed are separated by filtration, washed twice with acetonitrile cooled to a temperature in the vicinity of 4° C. (10 cc in total) and dried under reduced pressure (20 mm Hg; 2.7 kPa) at a temperature in the vicinity of 20° C. in the presence of potassium hydroxide pellets. A product (6.6 g), m.p. 148° C., is thereby obtained, which is dissolved in boiling isopropanol (100 cc). The solution obtained is cooled at a temperature in the vicinity of 4° C. for 2 hours. The crystals formed are separated by filtration, washed twice with isopropanol cooled to a temperature in the vicinity of 4° C. (20 cc) and then twice with diethyl ether (40 cc in total) and dried under reduced pressure (20 mm Hg; 2.7 kPa) at a temperature in the vicinity of 20° C. in the presence of potassium hydroxide pellets. N-[3-(3-methylphenoxy)phenyl]-3-(3-pyridyl)-1H,3H-pyrrolo[1,2-c]thiazole-7-carboxamide (5.5 g) in the form of cream-coloured crystals, m.p. 149° C., is thereby obtained.

The 3-(3-methylphenoxy)aniline may be prepared according to K. IKAWA, J. Pharm. Soc. Jap., 75, 457 (1955); Chem. Abstr., 50, 2480 (1956).

The 7-chloroformyl-3-(3-pyridyl)-1H,3H-pyrrolo[1,2-c]thiazole hydrochloride is prepared according to the method described in European patent No. 0,115,979.

EXAMPLE 7

7-Chloroformyl-3-(3-pyridyl)-1H,3H-pyrrolo[1,2-c]thiazole hydrochloride (12 g) is added, at a temperature between 60° and 70° C., to a solution of 3-(4-methylphenoxy)aniline (8 g) and triethylamine (8.1 g) in dioxane (200 cc) which is heated to a temperature in the vicinity of 60° C., in the course of 5 minutes. The suspension obtained is heated, with stirring, at a temperature in the vicinity of 100° C. for 7 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (300 cc) and the solution obtained is washed twice with distilled water (500 cc in total), twice with an aqueous 2N sodium hydroxide solution (300 cc in total) and twice with distilled water (500 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 60° C. A product (16.8 g) is thereby obtained, which is chromatographed on an 8 cm diameter column containing silica (0.02–0.045 mm; 640 g). Elution is carried out with ethyl acetate under a pressure of 0.4 bar (40 kPa), collecting 500 cc fractions. The first 5 fractions are discarded. The following 4 fractions are combined and concentrated to dryness under reduced pressure (20 mm Hg; 2.7 kPa) at a temperature in the vicinity of 60° C. A crude product (13 g) is thereby obtained, which is dissolved in a boiling mixture (40 cc) of cyclohexane and ethyl acetate (50:50 by volume). Decolourizing charcoal (0.5 g) is added to the solution obtained and the suspension is filtered in the heated state. The filtrate obtained is cooled at a temperature in the vicinity of 4° C. for 16 hours. The crystals formed are separated by filtration, washed twice with a mixture (50 cc) of cyclohexane and ethyl acetate (50:50 by volume) which is cooled to a temperature in the vicinity of 4° C. and twice with diethyl ether (50 cc in total) and then dried under reduced pressure (20 mm Hg; 2.7 kPa) at a temperature in the vicinity of 20° C. in the presence of potassium hydroxide pellets. N-[3-(4-methylphenoxy)phenyl]-3-(3-pyridyl)-1H,3H-pyrrolo[1,2-c]thiazole-7-carboxamide (8.9 g) in the form of white crystals, m.p. 110° C., is thereby obtained.

The 3-(4-methylphenoxy)aniline may be prepared according to the method described in Dutch patent No. 66/2,994.

The 7-chloroformyl-3-(3-pyridyl)-1H,3H-pyrrolo[1,2-c]thiazole hydrochloride is prepared according to the method described in European patent No. 0,115,979.

EXAMPLE 8

7-Chloroformyl-3-(3-pyridyl)-1H,3H-pyrrolo[1,2-c]thiazole hydrochloride (10 g) is added, at a temperature between 61° and 65° C., to a solution of 3-(2-methoxyphenoxy)aniline (7.1 g) and triethylamine (6.7 g) in dioxane (160 cc) which is heated to a temperature in the vicinity of 60° C., in the course of 30 minutes. The suspension obtained is heated, with stirring, at a temperature in the vicinity of 100° C. for 6 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (400 cc). The solution obtained is washed with distilled water (100 cc), twice with an aqueous 1N sodium hydroxide solution (200 cc in total), and 6 times with distilled water (600 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. A crude product (7.8 g) is thereby obtained, which is dissolved in boiling acetonitrile (50 cc). Decolourizing charcoal (0.5 g) is added to the solution obtained and the suspension is filtered in the heated state. The filtrate is cooled at a temperature in the vicinity of 4° C. for 1 hour. The crystals formed are separated by filtration, washed twice with acetonitrile cooled to a temperature in the vicinity of 4° C. (15 cc in total) and twice with diethyl ether (30 cc in total) and then dried under reduced pressure (20 mm Hg; 2.7 kPa) at a temperature in the vicinity of 20° C. in the presence of potassium hydroxide pellets. N-[3-(2-methoxyphenoxy)phenyl]-3-(3-pyridyl-1H,3H-pyrrolo[1,2-c]thiazole-7-carboxamide (3.9 g) in the form of white crystals, m.p. 163° C. is thereby obtained.

The 3-(2-methoxyphenoxy)aniline is prepared according to K. IKAWA, J. Pharm. Soc. Jap., 79, 1493 (1959); Chem. Abstr., 54, 10922 (1960).

The 7-chloroformyl-3-(3-pyridyl)-1H,3H-pyrrolo[1,2-c]thiazole hydrochloride is prepared according to the method described in European patent No. 0,115,979.

EXAMPLE 9

7-Chloroformyl-3-(3-pyridyl)-1H,3H-pyrrolo[1,2-c]thiazole hydrochloride (9 g) is added, at a temperature between 60° and 65° C., to a solution of 3-(3-methoxyphenoxy)aniline (6.45 g) and triethylamine (6.1 g) in dioxane (200 cc) which is heated to a temperature in the vicinity of 60° C., in the course of 15 minutes. The suspension obtained is heated, with stirring, at a temperature in the vicinity of 100° C. for 4 hours and 30 minutes and then stirred at a temperature in the vicinity of 20° C. for 16 hours. The solvent is evaporated off under reduced pressure (20 mm Hg; 2.7 kPa) at a temperature in the vicinity of 65° C. The residue is dissolved in methylene chloride (350 cc). The solution obtained is washed twice with distilled water (200 cc in total), twice with an aqueous 1N sodium hydroxide solution (200 cc in total) and 5 times with distilled water (750 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. A crude product (12 g) is thereby obtained, which is dissolved in boiling acetonitrile (50 cc). Decolourizing charcoal (0.5 g) is added to the solution obtained and the suspension is filtered in the heated state. The filtrate is cooled at a temperature in the vicinity of 4° C. for 2 hours. The crystals formed are separated by filtration, washed twice with acetonitrile cooled to a temperature in the vicinity of 4° C. (10 cc in total) and then dried under reduced pressure (20 mm Hg; 2.7 kPa) at a temperature in the vicinity of 20° C. in the presence of potassium hydroxide pellets. N-[3-(3-methoxyphenoxy)phenyl]-3-(3-pyridyl)-1H,3H-pyrrolo[1,2-c]thiazole-7-carboxamide (4.5 g) in the form of cream-coloured crystals, m.p. 130° C., is thereby obtained.

The 3-(3-methoxyphenoxy)aniline may be prepared according to K. IKAWA, J. Pharm. Soc. Jap., 79, 1493 (1959).

The 7-chloroformyl-3-(3-pyridyl)-1H,3H-pyrrolo[1,2-c]thiazole hydrochloride may be prepared according to the method described in European patent No. 0,115,979.

EXAMPLE 10

7-Chloroformyl-3-(3-pyridyl)-1H,3H-pyrrolo[1,2-c]thiazole hydrochloride (9 g) is added, at a temperature in the vicinity of 60° C., to a solution of 3-(4-methoxyphenoxy)aniline (6.45 g) and triethylamine (6.1 g) in dioxane (200 cc which is heated to a temperature in the vicinity of 60° C., in the course of 15 minutes. The suspension obtained is heated, with stirring, at a temperature in the vicinity of 100° C. for 5 hours and then stirred at a temperature in the vicinity of 20° C. for 12 hours. The solvent is evaporated off under reduced pressure (20 mm Hg; 2.7 kPa) at a temperature in the vicinity of 65° C. The residue is dissolved in methylene chloride (400 cc) and the solution obtained is washed twice with distilled water (200 cc in total), twice with an aqueous 1N sodium hydroxide solution (200 cc in total) and 5 times with distilled water (500 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. A product (12.5 g) is thereby obtained, which is chromatographed on a 3 cm diameter column containing silica (0.063–0.2 mm; 120 g). Elution is carried out with mixtures of methylene chloride and methanol, collecting 300 cc fractions. The first 5 fractions originating from elution with pure methylene chloride are discarded. The following 10 fractions originating from elution with a mixture of methylene chloride and methanol (99:1 by volume) are combined and concentrated to dryness under reduced pressure (20 mm Hg; 2.7 kPa) at a temperature in the vicinity of 50° C. A crude product (9.2 g) is thereby obtained, which is dissolved in boiling isopropanol (85 cc). Decolourizing charcoal (0.5 g) is added to the solution obtained and the suspension is filtered in the heated state. The filtrate obtained is cooled at a temperature in the vicinity of 4° C. for 16 hours. The crystals formed are separated by filtration, washed twice with isopropanol cooled to a temperature in the vicinity of 4° C. (20 cc) and twice with diethyl ether (40 cc in total) and then dried under reduced pressure (20 mm Hg; 2.7 kPa) at a temperature in the vicinity of 20° C. in the presence of potassium hydroxide pellets. N-[3-(4-methoxyphenoxy)phenyl]-3-(3-pyridyl)-1H,3H-pyrrolo[1,2-c]thiazole-7-carboxamide (5 g) in the form of cream-coloured crystals, m.p. 120° C., is thereby obtained.

The 3-(4-methoxyphenoxy)aniline may be prepared according to K. IKAWA, J. Pharm., Soc., Jap., 79, 1493 (1959).

The 7-chloroformyl-3-(3-pyridyl)-1H,3H-pyrrolo[1,2-c]thiazole hydrochloride is prepared according to the method described in European patent No. 0,115,979.

EXAMPLE 11

7-Chloroformyl-3-(3-pyridyl)-1H,3H-pyrrolo[1,2-c]thiazole hydrochloride (8.4 g) is added, at a temperature between 60° and 65° C., to a solution of 2-methoxy-5-phenoxyaniline (6 g) and triethylamine (5.7 g) in dioxane (100 cc) which is heated to a temperature in the vicinity of 60° C., in the course of 30 minutes. The suspension obtained is heated, with stirring, at a temperature in the vicinity of 100° C. for 6 hours and then stirred at a temperature in the vicinity of 20° C. for 16 hours. The solvent is evaporated off under reduced pressure (20 mm Hg; 2.7 kPa) at a temperature in the vicinity of 60° C. The residue is taken up with a mixture of aqueous 1N sodium hydroxide solution (150 cc) and methylene chloride (350 cc). The organic phase is separated, washed 5 times with distilled water (500 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. A crude product (9 g) is thereby obtained, which is suspended in a mixture (30 cc) of cyclohexane and ethyl acetate (50:50 by volume). The crystals formed are separated by filtration, washed twice with a mixture (10 cc in total) of cyclohexane and ethyl acetate (50:50 by volume) and then dried under reduced pressure (20 mm Hg; 2.7 kPa) at a temperature in the vicinity of 20° C. in the presence of potassium hydroxide pellets. A product (6.6 g) with a melting point of 148° C. is thereby obtained, which is dissolved in boiling acetonitrile (50 cc); decolourizing charcoal (0.5 g) is added to the solution obtained and the suspension is filtered in the heated state. The filtrate is cooled to a temperature in the vicinity of 4° C. for 16 hours. The crystals formed are separated by filtration, washed twice with acetonitrile cooled to a temperature in the vicinity of 4° C. (20 cc in total) and then dried under reduced pressure (20 mm Hg; 2.7 kPa) at a temperature in the vicinity of 20° C. in the presence of potassium hydroxide pellets. N-(2-methoxy-5-phenoxyphenyl)-3-(3-pyridyl)-1H,3H-pyrrolo[1,2-c]thiazole-7-carboxamide (5 g) in the form of white crystals, m.p. 158° C., is thereby obtained.

The 2-methoxy-5-phenoxyaniline may be obtained according to G. SCHIEMANN and W. WINKELMULLER, J. Prakt. Chem., 135, 101 (1932).

The 7-chloroformyl-3-(3-pyridyl)-1H,3H-pyrrolo[1,2-c]thiazole hydrochloride is prepared according to the method described in European patent No. 0,115,979.

EXAMPLE 12

7-Chloroformyl-3-(3-pyridyl)-1H,3H-pyrrolo[1,2-c]thiazole hydrochloride (12 g) is added, at a temperature between 60° and 68° C., to a solution of 3-(2-pyridyloxy)aniline (7.4 g) and triethylamine (8.1 g) in dioxane (200 cc) which is heated to a temperature in the vicinity of 60° C., in the course of 5 minutes. The suspension obtained is heated, with stirring, at a temperature in the vicinity of 100° C. for 7 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (300 cc). The solution obtained is washed twice with distilled water (500 cc in total), twice with an aqueous 1N sodium hydroxide solution (300 cc in total) and twice with distilled water (500 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 60° C. A crude product (15.8 g) is thereby obtained, which is dissolved in boiling acetonitrile (100 cc). Decolourizing charcoal (0.5 g) is added to the solution obtained and the suspension is filtered in the heated state. The filtrate is cooled at a temperature in the vicinity of 20° C. for 3 hours. The crystals formed are separated by filtration, washed 3 times with acetonitrile (45 cc in total) and 3 times with diethyl ether (90 cc in total) and then dried under reduced pressure (20 mm Hg; 2.7 kPa) at a temperature in the vicinity of 20° C. in the presence of potassium hydroxide pellets. N-[3-(2-pyridyloxy)phenyl]-3-(3-pyridyl)-1H,3H-pyrrolo[1,2-c]thiazole-7-carboxamide (8.5 g) in the form of cream-coloured crystals, m.p. 132° C., is thereby obtained.

The 3-(2-pyridyloxy)aniline may be prepared according to the method described in German patent No. 3,139,457.

The 7-chloroformyl-3-(3-pyridyl)-1H,3H-pyrrolo[1,2-c]thiazole hydrochloride is prepared according to the method described in European patent No. 0,115,979.

EXAMPLE 13

7-Chloroformyl-3-(3-pyridyl)-1H,3H-pyrrolo[1,2-c]thiazole hydrochloride (6 g) is added, at a temperature between 65° and 72° C., to a solution of 3-(3-pyridyloxy)aniline (3.9 g) and triethylamine (4.05 g) in dioxane (150 cc) which is heated to a temperature in the vicinity of 65° C., in the course of 5 minutes. The suspension obtained is heated, with stirring, at a temperature in the vicinity of 100° C. for 6 hours and 30 minutes and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (300 cc). The solution obtained is washed twice with distilled water (300 cc in total), twice with an aqueous 1N sodium hydroxide solution (300 cc in total) and twice with distilled water (300 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 60° C. A crude product (8.2 g) is thereby obtained, which is dissolved in boiling acetonitrile (50 cc). Decolourizing charcoal (0.5 g) is added to the solution obtained and the suspension is filtered in the heated state. The filtrate is cooled at a temperature in the vicinity of 20° C. for 2 hours. The crystals formed are separated by filtration, washed 3 times with acetonitrile (30 cc in total) and 3 times with diethyl ether (90 cc in total) and then dried under reduced pressure (20 mm Hg; 2.7 kPa) at a temperature in the vicinity of 20° C. in the presence of potassium hydroxide pellets. N-[3-(3-pyridyloxy)-phenyl]-3-(3-pyridyl)-1H, 3H-pyrrolo[1,2-c]thiazole-7-carboxamide (3.4 g) in the form of cream-coloured crystals, m.p. 154° C., is thereby obtained.

The 7-chloroformyl-3-(3-pyridyl)-1H,3H-pyrrolo[1,2-c]thiazole hydrochloride is prepared according to the method described in European patent No. 0,115,979.

The 3-(3-pyridyloxy)aniline is prepared as follows: ferric chloride (0.4 g) is added, at a temperature between 90° and 98° C., to a suspension of 3-(3-pyridyloxy)nitrobenzene (16.2 g) and iron powder (37.5 g) in distilled water (40 cc) which is heated to a temperature in the vicinity of 90° C. The suspension obtained is heated at a temperature in the vicinity of 98° C. for 1 hour and 15 minutes and then stirred at a temperature in the vicinity of 20° C. for 16 hours, treated with methylene chloride (550 cc) and distilled water (75 cc) and filtered. The organic phase is separated, dried over anhydrous magnesium sulphate, treated with decolourizing charcoal (0.5 g), filtered and concentrated to dryness under reduced pressure (20 mm Hg; 2.7 kPa) at a temperature in the vicinity of 60° C. A crude oil (13.1 g) is thereby obtained which is chromatographed on a 6 cm diameter column containing silica (0.02–0.045 mm; 450 g). Elution is carried out with mixtures of ethyl acetate and cyclohexane at a pressure of 0.4 bar (40 kPa), collecting 150 cc fractions. The first 15 fractions originating from elution with an ethyl acetate:cyclohexane (50:50 by volume) mixture are discarded. The following 5 fractions originating from elution with an ethyl acetate:cyclohexane (50:50 by volume) mixture and the following 5 fractions originating from elution with pure ethyl acetate are combined and concentrated to dryness under reduced pressure (20 mm Hg; 2.7 kPa) at a temperature in the vicinity of 60° C. 3-(3-pyridyloxy)aniline in the form of an orange-yellow liquid [Rf=0.25; silica gel thin layer chromatography; eluant: cyclohexane:ethyl acetate (50:50 by volume)] is thereby obtained.

The 3-(3-pyridyloxy)nitrobenzene is prepared as follows: a solution of 3-hydroxypyridine (47.5 g) and potassium hydroxide pellets (33 g) in ethanol (400 cc) is heated at a temperature in the vicinity of 80° C. for 1 hour. The solvent is evaporated off under reduced pressure (20 mm Hg; 2.7 kPa) at a temperature in the vicinity of 70° C. and the residue is dissolved in dimethyl sulphoxide (350 cc). 3-Bromonitrobenzene (101 g) and copper powder (0.1 g) are added to the solution obtained and the mixture is then heated under a dry nitrogen stream at a temperature in the vicinity of 160° C. for 1 hour. The reaction mixture obtained is cooled to a temperature in the vicinity of 20° C. and distilled water (2500 cc) and methylene chloride (500 cc) are added to it. The organic phase is separated and the aqueous phase is extrated twice with methylene chloride (1000 cc in total). The organic extracts are combined, washed 3 times with distilled water (1500 cc), dried over anhydrous magnesium sulphate, treated with decolourizing charcoal (0.5 g), filtered and concentrated to dryness under reduced pressure (20 mm Hg; 2.7 kPa) at a temperature in the vicinity of 60° C. The crude oil obtained (77 g) is distilled under reduced pressure. 3-(3-Pyridyloxy)nitrobenzene (41.8 g) in the form of an orange liquid, b.p. 165°–175° C. at 0.1 mm Hg (13.5 Pa), is thereby obtained.

EXAMPLE 14

7-Chloroformyl-3-(3-pyridyl)-1H,3H-pyrrolo[1,2-c]thiazole hydrochloride (24 g) is added, at a temperature in the vicinity of 65° C., to a solution of 3-aminobenzophenone (15.7 g) and triethylamine (16.1 g) in dioxane (400 cc) which is heated to a temperature in the vicinity of 65° C., in the course of 15 minutes. The suspension obtained is heated, with stirring, at a temperature in the vicinity of 100° C. for 6 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (500 cc) and the solution obtained is washed twice with distilled water (200 cc in total), 4 times with an aqueous 1N sodium hydroxide solution (800 cc in total) and 5 times with distilled water (500 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. The product obtained is chromatographed on an 8.5 cm diameter column containing silica (0.02–0.045 mm; 1 kg). Elution is carried out with mixtures of cyclohexane and ethyl acetate at a pressure of 0.4 bar (40 kPa), collecting 500 cc fractions. The first 10 fractions originating from elution with an ethyl acetate:cyclohexane (60:40 by volume) mixture and the following 5 fractions originating from elution with an ethyl acetate:cyclohexane (80:20 by volume) mixture are discarded. The following 10 fractions originating from elution with an ethyl acetate:cyclohexane (80:20 by volume) mixture and the following 2 fractions originating from elution with an ethyl acetate:cyclohexane (90:10 by volume) mixture are combined and concentrated to dryness under reduced pressure (20 mm Hg; 2.7 kPa) at a temperature in the vicinity of 50° C. A crude product (26.5 g) is thereby obtained, which is dissolved in boiling acetonitrile (150 cc). Decolourizing charcoal (0.5 g) is added to the solution obtained and the suspension is filtered in the heated state. The filtrate obtained is cooled at a temperature in the vicinity of 45° C. for 16 hours. The crystals formed are separated by filtration, washed 3 times with acetonitrile cooled to a temperature in the vicinity of 4° C. (90 cc in total) and 3 times with diethyl ether (90 cc in total) and then dried under reduced pressure (20 mm Hg; 2.7 kPa) at a temperature in the vicinity of 20° C. in the presence of potassium hydroxide pellets. N-(3-benzoylphenyl)-3-(3-pyridyl)-1H,3H-pyrrolo[1,2-c]thiazole-7-carboxamide (14 g) in the form of creamcoloured crystals, m.p. 154° C, is thereby obtained.

The 3-aminobenzophenone may be prepared according to R. GEIGY and W. KOENIGS, Ber., 18, 2400 (1885).

The 7-chloroformyl-3-(3-pyridyl)-1H,3H-pyrrolo[1,2-c]thiazole hydrochloride is prepared according to the method described in European patent No. 0,115,979.

EXAMPLE 15

7-Chloroformyl-3-(3-pyridyl)-1H,3H-pyrrolo[1,2-c]thiazole hydrochloride (6 g) is added, at a temperature between 66° and 72° C., to a solution of 3-amino-4'-chlorobenzophenone (4.6 g) and triethylamine (4.05 g) in dioxane (150 cc) which is heated to a temperature in the vicinity of 66° C., in the course of 5 minutes. The suspension obtained is heated, with stirring, at a temperature in the vicinity of 100° C. for 8 hours and then stirred at a temperature in the vicinity of 20° C. for 16 hours. The solvent is evaporated off under reduced pressure (20 mm Hg; 2.7 Kpa) at a temperature in the vicinity of 60° C. The residue is dissolved in methylene chloride (300 cc). The solution obtained is washed twice with distilled water (300 cc in total), twice with an aqueous 2N sodium hydroxide solution (300 cc in total) and twice with distilled water (300 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 60° C. A crude product (9.8 g) is thereby obtained, which is dissolved in boiling acetonitrile (250 cc). Decolourizing charcoal (0.5 g) is added to the solution obtained and the suspension is filtered in the heated state. The filtrate is cooled at a temperature in the vicinity of 10° C. for 3 hours. The crystals formed are separated by filtration, washed 3 times with acetonitrile (45 cc in total) and 3 times with diethyl ether (90 cc in total) and then dried under reduced pressure (20 mm Hg; 2.7 kPa) at a temperature in the vicinity of 20° C. in the presence of potassium hydroxide pellets. N-[3-(4-chlorobenzoyl)-phenyl]-3-(3-pyridyl)-1H,3H-pyrrolo[1,2-c]thiazole-7-carboxamide (3.2 g) in the form of pale yellow crystals, m.p. 176° C., is thereby obtained.

The 3-amino-4'-chlorobenzophenone may be obtained according to F.E. KING, T.J. KING and I.H.M. MUIR, J. Chem. Soc., 5, (1946).

The 7-chloroformyl-3-(3-pyridyl)-1H,3H-pyrrolo[1,2-c]thiazole hydrochloride is prepared according to the method described in European patent No. 0,115,979.

EXAMPLE 16

7-Chloroformyl-3-(3-pyridyl)-1H,3H-pyrrolo[1,2-c]thiazole hydrochloride (6 g) is added, at a temperature between 64° and 70° C., to a solution of 3-amino-3'-methylbenzophenone (4.25 g) and triethylamine (4.05 g) in dioxane (150 cc) which is heated to a temperature in the vicinity of 64° C., in the course of 5 minutes. The suspension obtained is heated, with stirring, at a temperature in the vicinity of 100° C. for 8 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (300 cc). The solution obtained is washed twice with distilled water (300 cc in total), twice with an aqueous 1N sodium hydroxide solution (300 cc in total) and twice with distilled water (300 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 60° C. A crude product (9 g) is thereby obtained, which is dissolved in boiling acetonitrile (75 cc). Decolourizing charcoal (0.5 g) is added to the solution obtained and the suspension is filtered in the heated state. The filtrate is cooled at a temperature in the vicinity of 10° C. for 3 hours. The crystals formed are separated by filtration, washed 3 times with acetonitrile cooled to a temperature in the vicinity of 4° C. (30 cc in total) and 3 times with diethyl ether (90 cc in total) and then dried under reduced pressure (20 mm Hg; 2.7 kPa) at a temperature in the vicinity of 20° C. in the presence of potassium hydroxide pellets. N-[3-(3-methylbenzoyl)phenyl]-3-(3-pyridyl)-1H, 3H-pyrrolo[1,2-c]thiazole-7-carboxamide (2.4 g) in the form of beige-coloured crystals, m.p. 164° C., is thereby obtained.

The 7-chloroformyl-3-(3-pyridyl)-1H,3H-pyrrolo[1,2-c]thiazole hydrochloride is prepared according to the method described in European patent No. 0,115,979.

The 3-amino-3'-methylbenzophenone may be prepared as follows: stannous chloride in the dihydrate form(19 g) is added, at a temperature between 40° and 80° C., to a suspension of 3'-methyl-3-nitrobenzophenone (6.8 g) in a mixture of ethanol (80 cc) and concentrated hydrochloric acid (30 cc), in the course of 10 minutes. The solution obtained is heated at a temperature in the vicinity of 85° C. for 3 hours and then stirred at a temperature in the vicinity of 20° C. for 16 hours. The solvent is evaporated off under reduced pressure (20 mm Hg; 2.7 kPa) at a temperature in the vicinity of 60° C. The residue is suspended in distilled water (300 cc). An aqueous 10N sodium hydroxide solution (100 cc) is added, at a temperature in the vicinity of 20° C., with stirring, to the suspension obtained and extraction is carried out 3 times with diethyl ether (550 cc in total). The ether extracts are combined, washed twice with distilled water (300 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. 3-Amino-3'-methylbenzophenone (5.7 g) in the form of yellow crystals, m.p. 110° C., is thereby obtained.

The 3'-methyl-3-nitrobenzophenone may be obtained according to K. DEY, C. EABORN and D.R.M. WALTON, Organometal Chem. Syn., 1, 151 (1971).

EXAMPLE 17

7-Chloroformyl-3-(3-pyridyl)-1H,3H-pyrrolo[1,2-c]thiazole hydrochloride (6 g) is added, at a temperature between 62° and 65° C., to a solution of 3-amino-4'-methoxybenzophenone (4.55 g) and triethylamine (4.05 g) in dioxane (100 cc) which is heated to a temperature in the vicinity of 62° C., in the course of 15 minutes. The suspension obtained is heated, with stirring, at a temperature in the vicinity of 100° C. for 5 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (200 cc) and the solution obtained is washed twice with distilled water (200 cc in total), twice with an aqueous 1N sodium hydroxide solution (200 cc in total) and 3 times with distilled water (300 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. A product (6.7 g) is thereby obtained, which is chromatographed on a 5.5 cm diameter column containing silica (0.02–0.045 mm; 500 g). Elution is carried out with ethyl acetate at a pressure of 0.4 bar (40 kPa), collecting 250 cc fractions. The first 9 fractions are discarded. The following 6 fractions are combined and concentrated to dryness under reduced pressure (20 mm Hg; 2.7 kPa) at a temperature in the vicinity of 50° C. A crude product (5 g) is thereby obtained. This product is dissolved in boiling acetonitrile (40 cc). Decolourizing charcoal (0.5 g) is added to the solution obtained and the suspension is filtered in the heated state. The filtrate obtained is cooled at a temperature in the vicinity of 4° C. for 2 hours. The crystals formed are separated by filtration, washed twice with acetonitrile cooled to a temperature in the vicinity of 4° C. (15 cc in total) and twice with diethyl ether (20 cc in total) and then dried under reduced pressure (20 mm Hg; 2.7 kPa) at a temperature in the vicinity of 20° C. in the presence of potassium hydroxide pellets. N-[3-(4-methoxybenzoyl)phenyl]-3-(3-pyridyl)-1H,3H-pyrrolo-[1,2-c]thiazole-7-carboxamide (3.9 g) in the form of creamcoloured crystals, m.p. 140° C., is thereby obtained.

The 3-amino-4'-methoxybenzophenone may be prepared according to H. OELSCHLAGER, Arzneim, Forsch., 8, 532 (1958).

The 7-chloroformyl-3-(3-pyridyl)-1H,3H-pyrrolo[1,2-c]thiazole hydrochloride is prepared according to the method described in European patent No. 0,115,979.

.EXAMPLE 18

7-Chloroformyl-3-(3-pyridyl)-1H,3H-pyrrolo[1,2-c]thiazole hydrochloride (6.9 g) is added, at a temperature between 50° and 85° C., to a solution of 3-(3-aminobenzoyl)pyridine (5.75 g) and triethylamine (4.65 g) in dioxane (120 cc) which is heated to a temperature in the vicinity of 50° C., in the course of 25 minutes. The suspension obtained is heated, with stirring, at a temperature in the vicinity of 100° C. for 6 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (350 cc) and the solution obtained is washed twice with distilled water (200 cc in total), twice with an aqueous 2N sodium hydroxide solution (200 cc in total) and 3 times with distilled water (450 cc) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. The product obtained is chromatographed on an 8 cm diameter column containing silica (0.02–0.045 mm; 500 g). Elution is carried out with mixtures of ethyl acetate and methanol at a pressure of 0.4 bar (40 kPa), collecting 500 cc fractions. The first 19 fractions originating from elution with pure ethyl acetate are discarded. The following 2 fractions originating from elution with pure ethyl acetate and the following 2 fractions originating from elution with an ethyl acetate:methanol (90:10 by volume) mixture are combined and concentrated to dryness under reduced pressure (20 mm Hg; 2.7 kPa) at a temperature in the vicinity of 50° C. A crude product (8 g) is thereby obtained. This product is dissolved in boiling acetonitrile (50 cc). Decolourizing chacoal (0.5 g) is added to the solution obtained and the suspension is filtered in the heated state. The filtrate obtained is cooled at a temperature in the vicinity of 4° C. for 1 hour. The crystals formed are separated by filtration, washed twice with acetonitrile cooled to a temperature in the vicinity of 4° C. (20 cc in total) and twice with diethyl ether (40 cc in total) and then dried under reduced pressure (20 mm Hg; 2.7 kPa) at a temperature in the vicinity of 20° C. in the presence of potassium hydroxide pellets. N-(3-nicotinoyl- phenyl)-3-(3-pyridyl)-1H,3H-pyrrolo[1,2-c]thiazole-7-carboxamide (4.9 g) in the form of cream-coloured crystals, m.p. 160° C., is thereby obtained.

The 3-(3-aminobenzoyl)pyridine may be obtained according to T. HOGBERG, B. ULFF, A.L. RENYI and S.B. ROSS, J. Med. Chem., 24, 1499 (1981).

The 7-chloroformyl-3-(3-pyridyl)-1H,3H-pyrrolo[1,2-c]thiazole hydrochloride is prepared according to the method described in European patent No. 0,115,979.

EXAMPLE 19

7-Chloroformyl-3-(3-pyridyl)-1H,3H-pyrrolo[1,2-c]thiazole hydrochloride (6 g), is added, at a temperature between 60° and 67° C., to a solution of 2-(3-aminobenzoyl) pyridine (3.95 g) and triethylamine (4.05 g) in dioxane (100 cc) which is heated to a temperature in the vicinity of 60° C., in the course of 15 minutes. The suspension obtained is heated, with stirring, at a temperature in the vicinity of 100° C. for 5 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (200 cc) and the solution obtained is washed twice with distilled water (200 cc in total), twice with an aqueous 1N sodium hydroxide solution (200 cc in total) and 3 times with distilled water (300 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. A product (3.7 g) is thereby obtained, which is chromatographed on a 5 cm diameter column containing silica (0.02–0.045 mm; 400 g). Elution is carried out with ethyl acetate at a pressure of 0.4 bar (40 kPa), collecting 400 cc fractions. The first 8 fractions are discarded. The following 5 fractions are combined and concentrated to dryness under reduced pressure (20 mm Hg; 2.7 kPa) at a temperature in the vicinity of 50° C. A crude product (1.9 g) is thereby obtained. This product is dissolved in boiling acetonitrile (13 cc). Decolourizing charcoal (0.5 g) is added to the solution obtained and the suspension is filtered in the heated state. The filtrate obtained is cooled at a temperature in the vicinity of 4° C. for 16 hours. The crystals formed are separated by filtration, washed twice with acetonitrile cooled to a temperature in the vicinity of 4° C. (6 cc in total) and twice with diethyl ether (20 cc in total) and then dried under reduced pressure (20 mm Hg; 2.7 kPa) at a temperature in the vicinity of 20° C. in the presence of potassium hydroxide pellets. N-[3-(2-pyridylcarbonyl)phenyl]-3-(3-pyridyl)-1H,3H-pyrrolo[1,2-c]thiazole-7carboxamide (1.4 g) in the form of cream-coloured crystals, m.p. 165° C., is thereby obtained.

The 7-chloroformyl-3-(3-pyridyl)-1H,3H-pyrrolo[1,2-c]thiazole hydrochloride is prepared according to the method described in European patent No. 0,115,979.

The 2-(3-aminobenzoyl)pyridine may be prepared as follows: Stannous chloride in the dihydrate form (63 g) is added, at a temperature in the vicinity of 3° C., to a suspension of 2-(3-nitrobenzoyl)pyridine (19 g) in a 3.7N solution (360 cc) of hydrogen chloride in ethanol, in the course of 45 minutes. The suspension obtained is stirred at a temperature in the vicinity of 4° C. for 1 hour and 30 minutes, at a temperature in the vicinity of 20° C. for 1 hour and 30 minutes and then at a temperature in the vicinity of 80° C. for 1 hour and 30 minutes. The solvent is evaporated off under reduced pressure (20 mm Hg; 2.7 kPa) at a temperature in the vicinity of 50° C. The residue is taken up with distilled water (200 cc). The aqueous solution is adjusted to a pH in the region of 11 by adding an aqueous 10N sodium hydroxide solution at a temperature in the vicinity of 25° C., saturated with sodium chloride and then extracted 3 times with diethyl ether (600 cc in total). The ether extracts are combined, washed 3 times with a saturated aqueous sodium chloride solution (300 cc in total), dried over anhydrous magnesium sulphate, treated with decolourizing charcoal (0.5 g), filtered and concentrated to dryness under reduced pressure (20 mm Hg; 2.7 kPa) at a temperature in the vicinity of 40° C. A crude product (15.8 g) is obtained, which is chromatographed on an 8 cm diameter column containing silica (0.02–0.045 mm; 500 g). Elution is carried out with a mixture of cyclohexane and ethyl acetate (50:50 by volume) at a pressure of 0.4 bar (40 kPa), collecting 400 cc fractions. The first 7 fractions are discarded. The following 7 fractions are combined and concentrated to dryness under reduced pressure (20 mm Hg; 2.7 kPa) at a temperature in the vicinity of 50° C. 2-(3-Aminobenzoyl) pyridine (12 g) in the form of a red oil is thereby obtained and it is used in the subsequent syntheses.

The 2-(3-nitrobenzoyl)pyridine may be prepared according to A.R. HANDS and A.R. KATRITZKY, J. Chem. Soc., 1754 (1958).

EXAMPLE 20

7-Chloroformyl-3-(3-pyridyl)-1H,3H-pyrrolo[1,2-c]thiazole hydrochloride (6 g) is added, at a temperature between 70° and 82° C., to a solution of 3-(2-thenoyl)aniline (4.1 g) and triethylamine (4.05 g) in dioxane (150 cc) which is heated to a temperature in the vicinity of 70° C., in the course of 10 minutes. The suspension obtained is heated, with stirring, at a temperature in the vicinity of 100° C. for 7 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (350 cc). The solution obtained is washed twice with distilled water (300 cc in total), twice with an aqueous 2N sodium hydroxide solution (300 cc in total) and twice with distilled water (300 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 60° C. A crude product (10 g) is thereby obtained, which is dissolved in boiling acetonitrile (250 cc). Decolourizing charcoal (0.5 g) is added to the solution obtained and the suspension is filtered in the heated state. The filtrate is cooled at a temperature in the vicinity of 4° C. for 16 hours. The crystals formed are separated by filtration, washed twice with acetonitrile (50 cc in total) and 3 times with diethyl ether (90 cc in total) and then dried under reduced pressure (20 mm Hg; 2.7 kPa) at a temperature in the vicinity of 20° C. in the presence of potassium hydroxide pellets. N-[3-(2-thenoyl)phenyl]-3-(3-pyridyl)1H,3H-pyrrolo[1,2-c]thiazole-7-carboxamide (5 g) in the form of cream-coloured crystals m.p. 172° C., is thereby obtained.

The 7-chloroformyl-3-(3-pyridyl)-1H,3H-pyrrolo[1,2-c]thiazole hydrochloride is prepared according to the method described in European patent No. 0,115,979.

The 3-(2-thenoyl)aniline may be prepared as follows: Stannous chloride in the dihydrate form (22.8 g) is added, at a temperature in the vicinity of 4° C., to a suspension of 3-(2-thenoyl)nitrobenzene (6.8 g) in a 3.7N solution (130 cc) of hydrogen chloride in ethanol, in the course of 40 minutes. After stirring at a temperature in the vicinity of 4° C. for 1 hour and then at a temperature in the vicinity of 20° C. for 1 hour, the solution obtained is heated at a temperature in the vicinity of 78° C. for 1 hour. The solvent is evaporated off under reduced pressure (20 mm Hg; 2.7 kPa) at a temperature in the vicinity of 50° C. The residue obtained is taken up with a mixture of distilled water (50 cc) and diethyl ether (100 cc), to which an aqueous 10N sodium hydroxide solution (130 cc) is added at a temperature in the vicinity of 15° C. The organic phase is separated and the aqueous phase is extracted 4 times with diethyl ether (400 cc in total). The ether extracts are combined, washed 3 times with distilled water (300 cc in total), dried over anhydrous magnesium sulphate, treated with decolourizing charcoal (0.5 g), and concentrated to dryness under reduced pressure (20 mm Hg; 2.7 kPa) at a temperature in the vicinity of 40° C. 2-(3-Thenoyl)aniline (5.7 g) in the form of yellow crystals m.p. 105° C., is thereby obtained.

The 2-(3-thenoyl)nitrobenzene may be prepared according to R. GONCALVES, M.R. KEGELMAN and E.V. BROWN, J. Org. Chem., 17, 705 (1952).

EXAMPLE 21

7-Chloroformyl-3-(3-pyridyl)-1H,3H-pyrrolo[1,2-c]thiazole hydrochloride (6 g) is added, at a temperature between 65° and 70° C., to a solution of 3-anilinoaniline (3.7 g) and triethylamine (4.05 g) in dioxane (150 cc) which is heated to a temperature in the vicinity of 65° C. in the course of 5 minutes. The suspension obtained is heated, with stirring, at a temperature in the vicinity of 100° C. for 7 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (300 cc). The solution obtained is washed twice with distilled water (300 cc in total), twice with an aqueous 2N sodium hydroxide solution (300 cc in total) and twice with distilled water (300 cc in total) and then dried over anhydrous magnesium sulphate, treated with decolourizing charcoal (0.5 g), filtered and concentrated to dryness under reduced pressure (20 ml Hg; 2.7 kPa) at a temperature in the vicinity of 60° C. A crude product (8.4 g) is thereby obtained, which is dissolved in boiling acetonitrile (50 cc). Decolourizing charcoal (0.5 g) is added to the solution obtained and the suspension is filtered in the heated state. The filtrate is cooled at a temperature in the vicinity of 4° C. for 16 hours. The crystals formed are separated by filtration, washed 3 times with acetonitrile (45 cc in total) and 3 times with diethyl ether (90 cc in total) and then dried under reduced pressure (20 mm Hg; 2.7 kPa) at a temperature in the vicinity of 20° C. in the presence of potassium hydroxide pellets. A product (0.3 g) with a melting point of 140° C. is thereby obtained. The crystallization motherliquors are concentrated to dryness under reduced pressure (20 mm Hg; 2.7 kPa) at a temperature in the vicinity of 60° C. A product (7.5 g) is thereby obtained, which is chromatographed on a 6 cm diameter column containing silica (0.02–0.045 mm; 480 g) eluting with an ethyl acetate: cyclohexane (80:20 by volume) mixture at a pressure of 0.4 bar (40 kPa) and collecting 200 cc fractions. The first 9 fractions are discarded. The following 9 fractions are combined and concentrated to dryness under reduced pressure (20 mm Hg; 2.7 kPa) at a temperature in the vicinity of 50° C. A product (5.2 g) is thereby obtained, which is combined with that obtained in the first crystallization and dissolved in boiling acetonitrile (55 cc). Decolourizing charcoal (0.5 g) is added to the solution obtained and the suspension is filtered in the heated state. The filtrate is cooled at a temperature in the vicinity of 4° C. for 16 hours. The crystals formed are separated by filtration, washed 3 times with acetonitrile cooled to a temperature in the vicinity of 4° C. (30 cc in total) and 3 times with diethyl ether (90 cc in total) and then dried under reduced pressure (20 mm Hg; 2.7 kPa) at a temperature in the vicinity of 20° C. in the presence of potassium hydroxide pellets. N-(3-anilinophenyl)-3-(3-pyridyl)-1H,3H-pyrrolo[1,2-c]thiazole-7-carboxamide (2.4 g) in the form of white crystals, m.p. 158° C., is thereby obtained.

The 3-anilinoaniline may be prepared according to H. WIELAND and W. RHEINHEIMER, Annalen, 423, 1 (1931).

7-Chloroformyl-3-(3-pyridyl)-1H,3H-pyrrolo[1,2-c]thiazole hydrochloride is prepared according to the method described in European patent No. 0,115,979.

EXAMPLE 22

7-Chloroformyl-3-(3-pyridyl)-1H,3H-pyrrolo[1,2-c]thiazole hydrochloride (5.7 g) is added, at a temperature between 60° and 65° C., to a solution of 3-benzylaniline (3.5 g) and triethylamine (3.9 g) in dioxane (100 cc) which is heated to a temperature in the vicinity of 60° C., in the course of 25 minutes. The suspension obtained is heated, with stirring, at a temperature in the vicinity of 100° C. for 6 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (250 cc). The solution obtained is washed twice with distilled water (160 cc in total), twice with an aqueous 1N sodium hydroxide solution (200 cc in total) and 5 times with distilled water (500 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. A crude product (5 g) is thereby obtained, which is dissolved in boiling acetonitrile (50 cc). Decolourizing charcoal (0.5 g) is added to the solution obtained and the suspension is filtered in the heated state. The filtrate is cooled at a temperature in the vicinity of 4° C. for 1 hour. The crystals formed are separated by filtration, washed with acetonitrile cooled to a temperature in the vicinity of 4° C. (10 cc) and twice with diethyl ether (20 cc in total) and then dried under reduced pressure (20 mm Hg; 2.7 kPa) at a temperature in the vicinity of 20° C. in the presence of potassium hydroxide pellets. N-(3-benzylphenyl)-3-(3-pyridyl)-1H,3H-pyrrolo[1,2-c]thiazole-7-carboxamide (2.4 g) in the form of white crystals, m.p. 139.5° C., is thereby obtained.

The 3-benzylaniline may be prepared according to H. OELSCHLAGER, Chem. Ber., 89, 2025 (1956).

The 7-chloroformyl-3-(3-pyridyl)-1H,3H-pyrrolo[1,2-c]thiazole hydrochloride is prepared according to the method described in European patent No. 0,115,979.

EXAMPLE 23

7-Chloroformyl-3-(3-pyridyl)-1H,3H-pyrrolo[1,2-c]thiazole hydrochloride (9 g) is added, at a temperature between 60° and 68° C., to a solution of 3-phenylthioaniline (6 g) and triethylamine (6.1 g) in dioxane (200 cc) which is heated to a temperature in the vicinity of 60° C., in the course of 5 minutes. The suspension obtained is heated, with stirring, at a temperature in the vicinity of 100° C. for 7 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (300 cc). The solution obtained is washed twice with distilled water (300 cc in total), twice with an aqueous 2N sodium hydroxide solution (300 cc in total) and twice with distilled water (300 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 60° C. A crude product (11.5 g) is thereby obtained, which is dissolved in boiling acetonitrile (110 cc). Decolourizing charcoal (0.5 g) is added to the solution obtained and the suspension is filtered in the heated state. The filtrate is cooled at a temperature in the vicinity of 10° C. for 1 hour. The crystals formed are separated by filtration, washed 3 times with acetonitrile (45 cc in total) and 3 times with diethyl ether (90 cc in total) and then dried under reduced pressure (20 mm Hg; 2.7 kPa) at a temperature in the vicinity of 20° C. in the presence of potassium hydroxide pellets. N-(3-phenylthiophenyl)-3-(3-pyridyl)-1H,3H-pyrrolo[1,2-c]thiazole-7-carboxamide (7.2 g) in the form of cream-coloured crystals, m.p. 152° C., is thereby obtained.

The 3-phenylthioaniline may be prepared according to the method described in Belgian patent No. 765,558.

The 7-chloroformyl-3-(3-pyridyl)-1H,3H-pyrrolo[1,2-c]thiazole hydrochloride is prepared according to the method described in European patent No. 0,115,979.

EXAMPLE 24

7-Chloroformyl-3-(3-pyridyl)-1H,3H-pyrrolo-1,2-c]thiazole hydrochloride (6 g) is added, at a temperature between 67° and 75° C., to a solution of 3-amino-4'-dimethylaminobenzophenone (4.8 g) and triethylamine (4.05 g) in dioxane (100 cc) which is heated to a temperature in the vicinity of 67° C., in the course of 20 minutes. The suspension obtained is heated, with stirring, at a temperature in the vicinity of 100° C. for 5 hours and 45 minutes and then stirred at a temperature in the vicinity of 20° C. for 16 hours. The solvent is evaporated off under reduced pressure (20 mm Hg; 2.7 kPa) at a temperature in the vicinity of 50° C. The residue is dissolved in methylene chloride (400 cc). The solution obtained is washed with distilled water (100 cc), with an aqueous 4N sodium hydroxide solution (100 cc) and 3 times with distilled water (450 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. A crude product (8.2 g) is thereby obtained, which is dissolved in boiling butan-1-ol (250 cc). Decolourizing charcoal (0.5 g) is added to the solution obtained and the suspension is filtered in the heated state. The filtrate is cooled at a temperature in the vicinity of 4° C. for 16 hours. The crystals formed are separated by filtration, washed twice with butan-1-ol (20 cc in total) and 3 times with diethyl ether (60 cc in total) and then dried under reduced pressure (20 mm Hg; 2.7 kPa) at a temperature in the vicinity of 20° C. in the presence of potassium hydroxide pellets. A product (2.8 g) which has a melting point of 204° C. is thereby obtained. The mother-liquors from crystallization and from washing are combined and concentrated to dryness under reduced pressure (20 mm Hg; 2.7 kPa) at a temperature in the vicinity of 50° C. A product (5.5 g) is obtained, which is taken up with boiling ethanol (50 cc). The suspension obtained is cooled at a temperature in the vicinity of 4° C. for 30 minutes. The crystals formed are separated by filtration, washed twice with ethanol (20 cc in total) and twice with diethyl ether (20 cc in total) and then dried in the vicinity of 20° C. in the presence of potassium hydroxide pellets. A product (2.5 g) with a melting point of 204° C. is thereby obtained, which is combined with the product (2.8 g) previously obtained and taken up with boiling acetonitrile (70 cc). The suspension obtained is cooled to a temperature in the vicinity of 20° C. and the crystals formed are separated by filtration, washed twice with acetonitrile (30 cc in total) and twice with ethanol (40 cc in total) and then dried under reduced pressure (20 mm Hg; 2.7 kPa) at a temperature in the vicinity of 20° C. in the presence of potassium hydroxide pellets. A product (4.9 g) with a melting point of 205° C. is thereby obtained. This product is dissolved in boiling butan-1-ol (150 cc). The solution obtained is filtered in the heated state and the filtrate is cooled at a temperature in the vicinity of 20° C. for 16 hours and then at a temperature in the vicinity of 4° C. for 48 hours. The crystals formed are separated by filtration, washed twice with butan-1-ol cooled to a temperature in the vicinity of 4° C. (10 cc in total), 3 times with ethanol cooled to a temperature in the vicinity of 4° C. (30 cc in total) and 3 times with diethyl ether (60 cc in total) and then dried under reduced pressure (20 mm Hg; 2.7 kPa) at a temperature in the vicinity of 20° C. in the presence of potassium hydroxide pellets. N-[3-(4-dimethylaminobenzoyl)phenyl]-3-(3-pyridyl)1H,3H-pyrrolo[1,2-c]-thiazole-7-carboxamide (4.6 g) in the form of cream-coloured crystals, m.p. 208° C. is thereby obtained.

The 7-chloroformyl-3-(3-pyridyl)-1H,3H-pyrrolo[1,2-c]thiazole hydrochloride is prepared according to the method described in European patent No. 0,115,979.

The 3-amino-4'-dimethylaminobenzophenone may be prepared as follows: Stannous chloride in the dihydrate form (29.3 g) is added, at a temperature between 44° and 79° C., to a suspension of 4'-dimethylamino-3-nitrobenzophenone (11.4 g) in a mixture of concentrated hydrochloric acid (45 cc) and ethanol (120 cc), in the course of 35 minutes. The solution obtained is heated at a temperature in the vicinity of 79° C. for 3 hours. The suspension obtained is concentrated under reduced pressure (20 mm Hg; 2.7 kPa) at a temperature in the vicinity of 50° C. The residue obtained is suspended in distilled water (350 cc) and an aqueous 10N sodium hydroxide solution (100 cc) is added, at a temperature in the vicinity of 5° C., to the suspension obtained and the mixture is stirred at a temperature in the vicinity of 20° C. for 30 minutes. The crystals formed are separated by filtration, washed 3 times with distilled water (60 cc in total) and air-dried. The crude product obtained is dissolved in boiling isopropanol (30 cc) and the solution obtained is cooled at a temperature in the vicinity of 4° C. for 2 hours. The crystals formed are separated by filtration, washed twice with isopropanol cooled to a temperature in the vicinity of 4° C. (20 cc in total) and twice with diethyl ether (40 cc) and then dried under reduced pressure (20 mm Hg; 2.7 kPa) at a temperature in the vicinity of 20° C. in the presence of potassium hydroxide pellets. 3-amino-4'-dimethylaminobenzophenone (8.4 g) in the form of beige-coloured crystals, m.p. 110° C., is thereby obtained.

The 4'-dimethylamino-3-nitrobenzophenone may be prepared according to R. C. SHAH, R. K. DESHPANDE and J. S. CHAUBAL, J. Chem. Soc., 642 (1932).

EXAMPLE 25

7-Chloroformyl-3-(3-pyridyl)-1H,3H-pyrrolo[1,2-c]thiazole hydrochloride (6 g) is added, at a temperature between 65° and 70° C., to a solution of 4-(3-aminobenzoyl)pyridine (4 g) and triethylamine (4.05 g) in dioxane (100 cc) which is heated to a temperature in the vicinity of 65° C., in the course of 15 minutes. The suspension obtained is heated, with stirring, at a temperature in the vicinity of 100° C. for 6 hours and 30 minutes and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (300 cc). The solution obtained is washed with distilled water (100 cc), with an aqueous 1N sodium hydroxide solution (100 cc) and 5 times with distilled water (500 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. A crude product (6.5 g) is thereby obtained, which is dissolved in boiling acetonitrile (300 cc). Decolourizing charcoal (0.5 g) is added to the solution obtained and the suspension is filtered in the heated state. The filtrate is cooled at a temperature in the vicinity of 4° C. for 16 hours. The crystals formed are separated by filtration, washed twice with acetonitrile cooled to a temperature in the vicinity of 4° C. (20 cc in total) and twice with diethyl ether (40 cc in total) and then dried under reduced pressure (20 mm Hg; 2.7 kPa) at a temperature in the vicinity of 20° C. in the presence of potassium hydroxide pellets. N-(3-isonicotinoylphenyl)-3-(3-pyridyl)-1H,3H-pyrrolo[1,2-c]thiazole7-carboxamide (5.5 g) in the form of white crystals, m.p. 186° C., is thereby obtained.

The 4-(3-aminobenzoyl)pyridine may be prepared according to F. SAUTER, P. STANETTY and A. MESBAH, Monatsh., 107, 1449 (1976).

The 7-chloroformyl-3-(3-pyridyl)-1H,3H-pyrrolo[1,2-c]thiazole hydrochloride is prepared according to the method described in European patent No. 0,115,979.

EXAMPLE 26

Hydrochloride of the acid chloride derived from (+)-3-(3-pyridyl)-1H,3H-pyrrolo[1,2-c]thiazole-7-carboxylic acid (5.4 g) is added, at a temperature between 60° and 62° C., to a solution of 3-amino-4-chlorobenzophenone (4.1 g) and triethylamine (3.65 g) in dioxane (80 cc) which is heated to a temperature in the vicinity of 60° C., in the course of 15 minutes. The suspension obtained is heated, with stirring, at a temperature in the vicinity of 100° C. for 5 hours and 40 minutes and then stirred at a temperature in the vicinity of 20° C. for 16 hours. The solvent is evaporated off under reduced pressure (20 mm Hg; 2.7 kPa) at a temperature in the vicinity of 50° C. The residue is dissolved in methylene chloride (250 cc). The solution obtained is washed twice with distilled water (200 cc in total), with an aqueous 2N sodium hydroxide solution (100 cc) and then 3 times with distilled water (300 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 45° C. A crude product (8.3 g) is thereby obtained, which is dissolved in boiling acetonitrile (50 cc). Decolourizing charcoal (0.5 g) is added to the solution obtained and the suspension is filtered in the heated state. The filtrate is cooled at a temperature in the vicinity of 4° C. for 1 hour. The crystals formed are separated by filtration, washed twice with acetonitrile cooled to a temperature in the vicinity of 4° C. (30 cc in total) and twice with diethyl ether (60 cc in total) and then dried under reduced pressure (20 mm Hg; 2.7 kPa) at a temperature in the vicinity of 20° C. in the presence of potassium hydroxide pellets. (+)-N-(2-chloro-5-benzoylphenyl)-3-(3-pyridyl)-1H,3H-pyrrolo[1,2-c]thiazole-7-carboxamide (3.7 g) in the form of cream-coloured crystals, m.p. 154° C., is thereby obtained.

$[\alpha]_D^{20} = +48.5° \pm 0.8°$ (c=0.86; dimethylformamide).

The hydrochloride of (+)-7-chloroformyl-3-(3-pyridyl)-1H,3H-pyrrolo[1,2-c]thiazole is prepared as described in Example 2.

The 3-amino-4-chlorobenzophenone may be prepared according to D. MARON and C. FOX, Ber., 47, 2774 (1914).

EXAMPLE 27

7-Chloroformyl-3-(3-pyridyl)-1H,3H-pyrrolo[1,2-c]thiazole hydrochloride (4.5 g) is added, at a temperature between 62° and 69° C., to a solution of 3'-amino-2-methoxybenzophenone (3.4 g) and triethylamine (3.05 g) in dioxane (90 cc) which is heated to a temperature in the vicinity of 62° C., in the course of 15 minutes. The suspension obtained is heated, with stirring, at a temperature in the vicinity of 100° C. for 6 hours and then stirred at a temperature in the vicinity of 20° C. for 16 hours. The solvent is evaporated off under reduced pressure (20 mm Hg; 2.7 kPa) at a temperature in the vicinity of 50° C. The residue is dissolved in methylene chloride (250 cc). The solution obtained is washed with distilled water (100 cc), twice with an aqueous 1N sodium hydroxide solution (200 cc in total) and 3 times with distilled water (300 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 45° C. A crude product (6.8 g) is thereby obtained, which is dissolved in boiling acetonitrile (60 cc). Decolourizing charocal (0.5 g) is added to the solution obtained and the suspension is filtered in the heated state. The filtrate is cooled at a temperature in the vicinity of 4° C. for 1 hour. The crystals formed are separated by filtration, washed twice with acetonitrile cooled to a temperature in the vicinity of 4° C. (30 cc in total) and 3 times with diethyl ether (60 cc in total) and then dried under reduced pressure (20 mm Hg; 2.7 kPa) at a temperature in the vicinity of 20° C. in the presence of potassium hydroxide pellets. N-[3-(2-methoxybenzoyl)phenyl]-3-(3-pyridyl)-1H,3H-pyrrolo[1,2-c]thiazole-7-carboxamide (4.1 g) in the form of white crystals, m.p. 184° C., is thereby obtained.

The 7-chloroformyl-3-(3-pyridyl)-1H,3H-pyrrolo[1,2-c]thiazole hydrochloride is prepared according to the method described in European patent No. 0,115,979.

The 3'-amino-2-methoxybenzophenone may be prepared as follows: Stannous chloride in the dihydrate form (10.3 g) is added, at a temperature between 62° and 66° C., to a suspension of 2-methoxy-3'-nitrobenzophenone (3.9 g) in a mixture of ethanol (40 cc) and concentrated (11.7N) hydrochloric adid (15.2 cc) which is heated to a temperature in the vicinity of 62° C., in the course of 5 minutes. The solution obtained is heated at a temperature in the vicinity of 80° C. for 4 hours, treated with stannous chloride in the dihydrate form (1 g) and heated at a temperature in the vicinity of 80° C. for a further period of 1 hour and then stirred at a temperature in the vicinity of 20° C. for 16 hours. The solvent is evaporated off under reduced pressure (20 mm Hg; 2.7 kPa) at a temperature in the vicinity of 50° C. The residue is dissolved in distilled water (40 cc) and the solution obtained is adjusted, while maintaining the temperature in the vicinity of 10° C., to a pH in the region of 13 by adding an aqueous 10N sodium hydroxide solution (50 cc) and then extracted 3 times with methylene chloride (150 cc in total). The organic extracts are combined, washed twice with distilled water (200 cc in total), dried over anhydrous magnesium sulphate, treated with decolourizing charcoal (0.5 g), filtered and concentrated to dryness under reduced pressure (20 mm Hg; 2.7 kPa at a temperature in the vicinity of 40° C. 3'- Amino-2-methoxybenzophenone (3.4 g) in the form of greenish yellow crystals, m.p. 81° C., is thereby obtained.

The 2-methoxy-3'-nitrobenzophenone may be prepared as follows: A suspension of 2-hydroxy-3'-nitrobenzophenone (3.6 g), potassium carbonate (4 g) and methyl iodide (4.2 g) in acetone (100 cc) is heated at a temperature in the vicinity of 56° C. for 16 hours. The solvent is evaporated off under reduced pressure (20 mm Hg; 2.7 kPa) at a temperature in the vicinity of 40° C. The solid obtained is dissolved in a mixture of distilled water (80 cc) and ethyl acetate (50 cc). The organic phase is separated and the aqueous phase is extracted twice with ethyl acetate; (100 cc in total). The organic extracts are combined, washed 3 times with distilled water (90 cc in total), dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. A crude product (3.8 g) is obtained, which is suspended in isopropyl ether (25 cc) at a temperature in the vicinity of 4° C. The crystals formed are separated by filtration, washed twice with isopropyl ether cooled to a temperature in the vicinity of 4° C. (10 cc in total) and then dried under reduced pressure (20 mm Hg; 2.7 kPa) at a temperature in the vicinity of 20° C. in the presence of potassium hydroxide pellets. 2-methoxy-3'-nitrobenzophenone (3.3 g) in the form of beige-coloured crystals, m.p. 94° C. is thereby obtained.

The 2-hydroxy-3'-nitrobenzophenone may be obtained according to I. H. BOWEN and J. R. LEWIS, J. Chem. Soc., Perkin Trans., I, 683 (1972).

EXAMPLE 28

7-Chloroformyl-3-(3-pyridyl)-1H,3H-pyrrolo[1,2-c]thiazole hydrochloride (8.8 g) is added, at a temperature between 60° and 75° C., to a solution of 3-cinnamoylaniline (6.57 g) and triethylamine (5.95 g) in dioxane (165 cc) which is heated to a temperature in the vicinity of 60° C., in the course of 10 minutes. The suspension obtained is heated, with stirring, at a temperature in the vicinity of 100° C. for 6 hours and 30 minutes and then stirred at a temperature in the vicinity of 20° C. for 16 hours. The solvent is evaporated off under reduced pressure (20 mm Hg; 2.7 kPa) at a temperature in the vicinity of 50° C. The residue is dissolved in methylene chloride (500 cc). The solution obtained is washed 4 times with distilled water (650 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 50° C. A crude product (13.5 g) is thereby obtained, which is dissolved in boiling acetonitrile (300 cc). Decolourizing charcoal (0.5 g) is added to the solution obtained and the suspension is filtered in the heated state. The filtrate is cooled at a temperature in the vicinity of 4° C. for 16 hours. The crystals formed are separated by filtration, washed 3 times with acetonitrile (60 cc in total) and then dried under reduced pressure (20 mm Hg; 2.7 kPa) at a temperature in the vicinity of 20° C. in the presence of potassium hydroxide pellets. N-(3- cinnamoylphenyl)-3-(3-pyridyl)-1H,3H-pyrrolo[1,2-c]thiazole -7-carboxamide (7.1 g) in the form of beige-coloured crystals, m.p. 190° C., is thereby obtained.

The 3-cinnamoylaniline may be prepared according to W. DAVEY and J. R. GWILT, J. Chem. Soc., 1008 (1957).

The 7-chloroformyl-3-(3-pyridyl)-1H,3H-pyrrolo[1,2-c]thiazole hydrochloride is prepared according to the method described in European patent No. 0,115,979.

EXAMPLE 29

7-Chloroformyl-3-(3-pyridyl)-1H,3H-pyrrolo[1,2-c]thiazole hydrochloride (5.1 g) is added, at a temperature between 70° and 78° C., to a solution of ethyl 2-(3'-aminobenzoyl)benzoate (4.6 g) and triethylamine (3.45 g) in dioxane (150 cc) which is heated to a temperature in the vicinity of 70° C., in the course of 5 minutes. The suspension obtained is heated, with stirring, at a temperature in the vicinity of 100° C. for 6 hours and 45 minutes and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (300 cc). The solution obtained is washed twice with distilled water (300 cc in total), twice with a saturated aqueous sodium bicarbonate solution (300 cc in total) and twice with distilled water (300 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 60° C. A crude product (9 g) is thereby obtained, which is chromatographed on an 8 cm diameter column containing silica (0.02–0.045 mm; 640 g). Elution is carried out with ethyl acetate at a pressure of 0.45 bar (45 kPa), collecting 300 cm fractions. The first 12 fractions are discarded. The following 6 fractions are combined and concentrated to dryness under reduced pressure (20 mm Hg; 2.7 kPa) at a temperature in the vicinity of 50° C. A crude product (5.1 g) is thereby obtained, which is dissolved in boiling acetonitrile (30 cc). The solution obtained is filtered in the heated state. The filtrate obtained is cooled at a temperature in the vicinity of 4° C. for 1 hour. The crystals formed are separated by filtration, washed 3 times with acetonitrile cooled to a temperature in the vicinity of 4° C. (30 cc in total) and 3 times with diethyl ether (90 cc in total) and the dried under reduced pressure (20 mm Hg; 2.7 kPa) at a temperature in the vicinity of 20° C. in the presence of potassium hydroxide pellets. N-[3-(2-ethoxycarbonylbenzoyl)phenyl]-3-(3-pyridyl)-1H,3H-pyrrolo[1,2-c]thiazole-7-carboxamide (1.2 g) in the form of cream-coloured crystals, m.p. 150° C., is thereby obtained.

The ethyl 2-(3'-aminobenzoyl)benzoate may be obtained according to the method described in German patent No. 279,201 (Beilstein, 14, 661).

The 7-chloroformyl-3-(3-pyridyl)-1H,3H-pyrrolo[1,2-c]thiazole hydrochloride is prepared according to the method described in European patent No. 0,115,979.

EXAMPLE 30

A solution of N-[3-(2-ethoxycarbonylbenzoyl)-phenyl]- 3-(3-pyridyl)-1H,3H-pyrrolo[1,2-c]thiazole-7-carboxamide (4.4 g) and potassium hydroxide pellets (1.8 g) in a mixture of ethanol (100 cc) and distilled water (50 cc) is stirred at a temperature in the vicinity of 20° C. for 3 hours. The solvent is evaporated off under reduced pressure (20 mm Hg; 2.7 kPa) at a temperature in the vicinity of 60° C. The residue is dissolved in distilled water (350 cc) and the solution obtained is adjusted to a pH in the region of 4 by adding an aqueous 4N acetic acid solution. The crystals formed are separated by filtration, washed 5 times with distilled water (500 cc in total) and dried under reduced pressure (20 mm Hg; 2.7 kPa) at a temperature in the vicinity of 20° C. in the presence of potassium hydroxide pellets. A crude product (3.5 g) is thereby obtained, which is dissolved in a boiling mixture (200 cc) of butan-1-ol and dimethylformamide (35:65 by volume). Decolourizing charcoal (0.5 g) is added to the solution obtained and the suspension is filtered in the heated state. The filtrate is cooled at a temperature in the vicinity of 4° C. for 3 days. The crystals formed are separated by filtration, washed 3 times with a mixture (30 cc in total) of butan-1-ol and dimethylformamide (35:65 by volume), 3 times with ethanol (90 cc in total) and 3 times with diethyl ether (90 cc in total) and then dried under reduced pressure (20 mm Hg; 2.7 kPa) at a temperature in the vicinity of 20° C. in the presence of potassium hydroxide pellets. N-[3-(2-carboxybenzoyl) phenyl]-3-(3-pyridyl)-1H,3H-pyrrolo[1,2-c]thiazole-7-carboxamide (1.8 g) in the form of white crystals, m.p. 315° C. is thereby obtained.

The N-[3-(2-ethoxycarbonylbenzoyl)phenyl]-3-(3-pyridyl)-1H,3H-pyrrolo[1,2-c]thiazole-7-carboxamide is prepared as in Example 29.

EXAMPLE 31

7-Chloroformyl-3-(3-pyridyl)-1H,3H-pyrrolo[1,2-c]thiazole hydrochloride (6 g) is added, at a temperature between 70° and 76° C., to a solution of 3-amino-4-dimethylaminobenzophenone (4.8 g) and triethylamine (4.05 g) in dioxane (150 cc) which is heated to a temperature in the vicinity of 70° C., in the course of 5 minutes. The suspension obtained is heated, with stirring, at a temperature in the vicinity of 100° C. for 7 hours and 10 minutes and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (300 cc). The solution obtained is washed twice with distilled water (300 cc in total), twice with an aqueous 1N sodium hydroxide solution (300 cc in total) and twice with distilled water (300 cc in total) and then dried over anhydrous magnesium sulphate, treated with decolourizing charcoal (0.5 g), filtered and concentrated to dryness under reduced pressure (20 mm Hg; 2.7 kPa) at a temperature in the vicinity of 60° C. A crude product (10.1 g) is thereby obtained, which is dissolved in boiling acetonitrile (80 cc). Decolourizing charcoal (0.5 g) is added to the solution obtained and the suspension is filtered in the heated state. The filtrate is cooled at a temperature in the vicinity of 20° C. for 2 hours. The crystals formed are separated by filtration, washed twice with acetonitrile (50 cc in total) and 3 times with diethyl ether (90 cc in total) and then dried under reduced pressure (20 mm Hg; 2.7 kPa) at a temperature in the vicinity of 20° C. in the presence of potassium hydroxide pellets. N-(5-benzoyl-2-dimethylaminophenyl)-3-(3-pyridyl)-1H,3H-pyrrolo[1,2-c]thiazole-7-carboxamide (2.4 g) in the form of yellow crystals, m.p. 186° C., is thereby obtained.

The 7-chloroformyl-3-(3-pyridyl)-1H,3H-pyrrolo[1,2-c]thiazole hydrochloride is prepared according to the method described in European patent No. 0,115,979.

The 3-amino-4-dimethylaminobenzophenone is prepared as follows: Hydrogen is bubbled through a suspension of 4-dimethylamino-3-nitrobenzophenone (5.4 g) and activated Raney nickel (2.7 g) in ethyl acetate (100 cc), for 3 hours at a temperature in the vicinity of 20° C. The suspension is filtered and the filtrate is concentrated to dryness under reduced pressure (20 mm Hg; 2.7 kPa) at a temperature in the vicinity of 60° C. The product thus obtained (5 g) is dissolved in a mixture (200 cc) of ethyl acetate and cyclohexane (40:60 by volume). The solution obtained is poured onto a 4 cm diameter column containing silica (0.02–0.045 mm; 10 g). The eluate is concentrated to dryness under reduced pressure (20 mm Hg; 2.7 kPa) at a temperature in the vicinity of 60° C. 3-Amino-4-dimethylaminobenzophenone (4.8 g) in the form of an orange-coloured oil [Rf =0.6; silica gel thin layer chromatography; eluant: cyclohexane:ethyl acetate (60:40 by volume)], is thereby obtained.

The 4-dimethylamino-3-nitrobenzophenone is prepared according to D. MARON and C. FOX, Ber., 47, 2774 (1914).

The present invention also provides a pharmaceutical composition which comprises a compound of general formula (I) or pharmaceutically acceptable salt thereof and a compatible and pharmaceutically acceptable diluent or adjuvant. The composition may also contain other pharmaceutically compatible products which may be inert or physiologically active. The pharmaceutical products may be administered orally, parenterally, rectally or locally.

Tablets, pills, powders (especially in gelatin capsules or wafer capsules) or granules may be used as solid compositions for oral administration. In these compositions, the compound according to the invention is mixed with one or more inert diluents such as starch, cellulose, sucrose, lactose or silica. These compositions may also contain substances other than diluents, e.g. one or more lubricants such as magnesium stearate or talcum, a colour, a coating (dragees) or a lacquer.

Pharmaceutically acceptable solutions, suspensions, emulsions, syrups and elixirs containing inert diluents such as water, ethanol, glycerol, vegetable oils or liquid paraffin may be used as liquid compositions for oral administration. These compositions may also contain substances other than diluents, e.g. wetting agents, sweeteners, thickeners, flavouring agents or stabilizers.

Sterile compositions for parenteral administration may preferably be aqueous or non-aqueous solutions, suspensions or emulsions. Water, propylene glycol, polyethylene glycol, vegetable oils, especially olive oil, injectable organic esters, e.g. ethyl oleate or other suitable organic solvents may be used as the solvent or the vehicle.

These compositions may also contain adjuvants, especially wetting agents, tonicity regulating agents, emulsifiers, dispersants and stabilizers. The sterilization may be carried out in several ways, e.g. by aseptizing filtration, by incorporating sterilizing agents into the composition, by radiation or by heating. They may also be prepared in the form of sterile solid compositions which may be dissolved in an injectable sterile medium at the time of use.

The compositions for rectal administration are suppositories or rectal capsules, which contain, in addition to the active product, excipients such as cocoa butter, semisynthetic glycerides or polyethylene glycols.

The compositions for local application may be e.g. creams, ointments, lotions, eye lotions, mouthwashes, nasal drops or aerosols.

In human therapeutics the pharmaceutical products according to the invention are particularly useful in the treatment of all pathological conditions in which PAF-acether may be directly or indirectly implicated, especially allergic and inflammatory conditions and complaints of the digestive system such as ulcers, colitises and intestinal lesions caused by radiation or endotoxin-induced shocks.

The doses depend on the effect sought and the period of treatment; they are generally between 25 and 300 mg per day, taken in a single dose or in split doses, by the oral or the intravenous route or by inhalation, for an adult.

In general, the medical practitioner will determine the dose that he considers most appropriate depending on age, weight and all the other factors specific to the subject under treatment.

The following examples, given in a non-limiting way, illustrate the compositions according to the invention.

EXAMPLE A

Tablets containing a 25 mg dose of the active product, with the following composition, are prepared according to the conventional technique:

| | |
|---|---|
| N—(3-phenoxyphenyl)-3-(3-pyridyl)-1H,3H—pyrrolo[1,2-c]thiazole-7-carboxamide | 25 mg |
| starch | 60 mg |
| lactose | 50 mg |
| magnesium stearate | 2 mg |

EXAMPLE B

Tablets containing a 25 mg dose of the active product, with the following composition, are prepared according to the conventional technique:

| | |
|---|---|
| (+)-N—(3-benzoylphenyl)-3-(3-pyridyl)-1H,3H—pyrrolo[1,2-c]thiazole-7-carboxamide | 25 mg |
| starch | 60 mg |
| lactose | 50 mg |
| magnesium stearate | 2 mg |

EXAMPLE C

An injectable solution containing 5 mg of the active product, with the following composition, is prepared according to the conventional technique:

| | |
|---|---|
| N—[(3-pyridyloxy)phenyl]-3-(3-pyridyl)-1H,3H—pyrrolo[1,2-c]thiazole-7-carboxamide | 5 mg |
| 0.1 N hydrochloric acid solution | 0.25 cc |
| injectable aqueous solution qs | 2 cc |

We claim:

1. A compound of the general formula I;

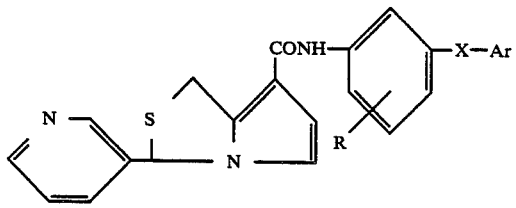

in which R is hydrogen or a halogen or an alkyl, alkyloxy amino, alkylamino or dialkylamino, group, X is oxygen or sulphur or an imino, carbonyl, carbonylmethylene, or vinylenecarbonyl group, or X represents a valency bond or a straight-chain alkylene group containing 1 to 4 carbon atoms and Ar is a phenyl, naphthyl, pyridyl, or thienyl group, it being possible for the group Ar to be unsubstituted or substituted with one or more halogen or alkyl, alkyloxy, amino, alkylamino, dialkylamino, carboxy or alkyloxycarbonyl group;
   each alkyl moiety containing 1 to 4 carbon atoms in a straight or branched chain; the compound being in separate enantiomeric form or mixtures thereof or a pharmaceutically acceptable salt thereof.

2. A compound as claimed in claim 1 in which R is hydrogen, halogen or an alkoxy or dialkylamino group, X is oxygen or sulphur or a methylene, imino, carbonyl, carbonylmethylene or vinylenecarbonyl group, and Ar is a phenyl naphthyl, pyridyl or 2-thienyl group, the group Ar being unsubstituted or substituted by one or more halogen or alkyl, alkoxy, dialkylamino, carboxy or alkyloxycarbonyl group.

3. A compound as claimed in claim 1 in which R is hydrogen, X is oxygen or a carbonyl group, and Ar is a phenyl or pyridyl group, Ar being unsubstituted or substituted by one or more halogen, or alkyl or alkyloxy group.

4. A compound as claimed in claim 1 in dextrorotatory form.

5. A compound according to claim 1 which is (+)-N-(3-benzoylphenyl)-3-(3-pyridyl)-1H,3H-pyrrolo[1,2-c]thiazole-7-carboxamide.

6. A compound according to claim 1 which is N-(3-benzoylphenyl)-3-(3-pyridyl)-1H,3H-pyrrolo[1,2-c]thiazole-7-carboxamide or a pharmaceutically acceptable salt thereof.

7. A compound according to claim 1 which is N-(3-phenoxyphenyl)-3-(3-pyridyl)-1H,3H-pyrrolo-[1,2-c]thiazole-7-carboxamide or a pharmaceutically acceptable salt thereof.

8. A compound according to claim 1 which is N-[3-(2-methylphenoxy)phenyl]-3-(3-pyridyl)-1H,3H-pyrrolo[1,2-c]thiazole-7-carboxamide or a pharmaceutically acceptable salt thereof.

9. A compound according to claim 1 which is N-[3-(3-[pyridyloxy)phenyl]-3-(3-pyridyl)-1H,3H-pyrrolo[1,2-c]thiazole-7-carboxamide or a pharmaceutically acceptable salt thereof.

10. A compound according to claim 1 which is N-[3-(3-methylphenoxy)phenyl]-3-(3-pyridyl)-1H,3H-pyrrolo[1,2-c thiazole-7-carboxamide or a pharmaceutically acceptable salt thereof.

11. A compound according to claim 1 which is N-[3-(3-methylbenzoyl)phenyl]-3-(3-pyridyl)-1H,3H-pyrrolo[1,2-c]thiazole-7-carboxamide or a pharmaceutically acceptable salt thereof.

12. A compound according to claim 1 which is N-[3-(4-chlorophenoxy)phenyl]-3-(3-pyridyl)-1H,3H-pyrrolo[1,2-c]thiazole-7-carboxamide or a pharmaceutically acceptable salt thereof.

13. A compound according to claim 1 which is N-[3-nicotinoylphenyl]-3-(3-pyridyl)-1H, 3H-pyrrolo [1, 2-c]thiazole-7-carboxamide or a pharmaceutically acceptable salt thereof.

14. A pharmaceutical composition for treatment of undesirable effects of PAF acether which comprises a compound as claimed in claim 1 and a compatible and pharmaceutically acceptable diluent or adjuvant.

15. A method of treatment of undesirable effects of P.A.F.-acether comprising administering to a subject suffering therefrom or liable thereto, an effective dose of a compound as claimed in claim 1.

16. A method of treatment of undesirable effects of P.A.F.-acether comprising administering to a subject suffering therefrom or liable thereto an effective dose of a composition as claimed in claim 14.

17. A method according to claim 16 in which the dose is from 25 to 300 mg per day of compound of general formula I or pharmaceutically acceptable salt thereof.

18. A method according to claim 16 in which the treatment is administered orally, intravenously or by inhalation.

* * * * *